(12) United States Patent
Haarala et al.

(10) Patent No.: US 9,616,196 B2
(45) Date of Patent: Apr. 11, 2017

(54) CATHETER SYSTEM WITH ATTACHABLE CATHETER HUB

(71) Applicant: Covidien LP, Mansfield, MA (US)

(72) Inventors: Brett Haarala, Framingham, MA (US); Richard Braga, North Easton, MA (US); Robert Frechette, Lakeville, MA (US); Kurt Haggstrom, Huntington Beach, CA (US)

(73) Assignee: Covidien LP, Mansfield, MA (US)

( * ) Notice: Subject to any disclaimer, the term of this patent is extended or adjusted under 35 U.S.C. 154(b) by 549 days.

(21) Appl. No.: 13/661,757

(22) Filed: Oct. 26, 2012

(65) Prior Publication Data

US 2013/0303966 A1    Nov. 14, 2013

Related U.S. Application Data

(60) Continuation of application No. 12/764,602, filed on Apr. 21, 2010, now Pat. No. 8,529,544, which is a
(Continued)

(51) Int. Cl.
*A61M 25/00* (2006.01)
*A61M 25/01* (2006.01)
*A61M 1/36* (2006.01)

(52) U.S. Cl.
CPC ...... *A61M 25/0026* (2013.01); *A61M 1/3661* (2014.02); *A61M 25/0097* (2013.01);
(Continued)

(58) Field of Classification Search
CPC ........ A61M 25/0097; A61M 2037/003; A61M 2025/0681; A61M 39/10; A61M 39/1011;
(Continued)

(56) References Cited

U.S. PATENT DOCUMENTS 3,456,965 A * 7/1969 Harrison ............. A61M 1/3655
24/324
4,214,779 A    7/1980 Losell
(Continued)

FOREIGN PATENT DOCUMENTS

WO    2005089851 A1    9/2005

OTHER PUBLICATIONS

Extended European Search Report from copending European Patent Application No. 08731290.6 mailed Aug. 31, 2011.
(Continued)

*Primary Examiner* — Bhisma Mehta
*Assistant Examiner* — Brandy S Lee
(74) *Attorney, Agent, or Firm* — Kenneth Collier; Jessica Kwak Rauckman

(57) ABSTRACT

A hemodialysis catheter assembly adapted for use in a subcutaneous tunneling procedure incorporates a mechanism for securing the catheter hub member to the elongated catheter, and to provide the requisite fluid communication between fluid passages within the hub and the catheter lumens within the catheter. The catheter hub member may be connected to the elongated catheter after implantation of the catheter via a subcutaneous tunneling procedure.

12 Claims, 33 Drawing Sheets

Related U.S. Application Data division of application No. 12/041,563, filed on Mar. 3, 2008, now Pat. No. 7,731,708.

(60) Provisional application No. 60/904,459, filed on Mar. 2, 2007.

(52) U.S. Cl.
CPC ..... *A61M 25/0194* (2013.01); *A61M 25/0028* (2013.01); *A61M 2025/0031* (2013.01); *A61M 2025/0034* (2013.01); *A61M 2025/0037* (2013.01)

(58) Field of Classification Search
CPC .......... A61M 2039/1033; A61M 25/00; A61M 2039/1027; A61M 2039/267; A61M 39/105; A61M 39/20; A61M 25/0014; A61M 2005/3206; A61M 25/0026; A61M 1/3661; A61M 2025/0031; A61M 2025/0034; A61M 2025/0037; A61M 25/0028; A61M 25/0194
USPC .......................................... 604/523, 533, 535
See application file for complete search history.

(56) References Cited

U.S. PATENT DOCUMENTS

| | | | |
|---|---|---|---|
| 4,795,197 A * | 1/1989 | Kaminski | F16L 25/0045 285/12 |
| 5,209,723 A | 5/1993 | Twardowski et al. | |
| 5,279,597 A | 1/1994 | Dassa et al. | |
| 5,401,245 A | 3/1995 | Haining | |
| 5,405,320 A | 4/1995 | Twardowski et al. | |
| 5,505,714 A | 4/1996 | Dassa et al. | |
| 5,509,897 A | 4/1996 | Twardowski et al. | |
| 5,624,413 A | 4/1997 | Markel et al. | |
| 5,636,875 A | 6/1997 | Wasser | |
| 5,897,499 A | 4/1999 | Machida | |
| 6,155,610 A * | 12/2000 | Godeau | F16L 25/0045 285/242 |
| 6,638,242 B2 | 10/2003 | Wilson et al. | |
| D498,844 S | 11/2004 | Diamond et al. | |
| 6,858,019 B2 | 2/2005 | McGuckin, Jr. et al. | |
| 6,872,198 B1 | 3/2005 | Wilson et al. | |
| 6,916,051 B2 | 7/2005 | Fisher | |
| 6,921,396 B1 | 7/2005 | Wilson et al. | |
| 6,969,381 B2 | 11/2005 | Voorhees | |
| 7,163,531 B2 | 1/2007 | Seese et al. | |
| 7,182,746 B2 | 2/2007 | Haarala et al. | |
| 7,261,708 B2 | 8/2007 | Raulerson | |
| 7,300,430 B2 | 11/2007 | Wilson et al. | |
| 7,377,915 B2 | 5/2008 | Rasmussen et al. | |
| 2003/0088213 A1 * | 5/2003 | Schweikert et al. | 604/177 |
| 2004/0065333 A1 | 4/2004 | Wilson et al. | |
| 2004/0092863 A1 | 5/2004 | Raulerson et al. | |
| 2004/0097903 A1 * | 5/2004 | Raulerson | 604/523 |
| 2004/0167478 A1 | 8/2004 | Mooney et al. | |
| 2004/0171997 A1 | 9/2004 | Wilson et al. | |
| 2005/0107770 A1 | 5/2005 | Schweikert et al. | |
| 2005/0137580 A1 | 6/2005 | Raulerson et al. | |
| 2005/0209581 A1 * | 9/2005 | Butts et al. | 604/523 |
| 2005/0209583 A1 | 9/2005 | Powers et al. | |
| 2005/0256461 A1 | 11/2005 | DiFiore et al. | |
| 2005/0261665 A1 | 11/2005 | Voorhees | |
| 2005/0267400 A1 | 12/2005 | Haarala et al. | |
| 2005/0273084 A1 | 12/2005 | Hinman et al. | |
| 2006/0015086 A1 | 1/2006 | Rasmussen et al. | |
| 2006/0095062 A1 | 5/2006 | Stephens | |
| 2006/0276773 A1 | 12/2006 | Wilson et al. | |
| 2007/0016167 A1 * | 1/2007 | Smith et al. | 604/533 |
| 2007/0060866 A1 | 3/2007 | Raulerson et al. | |
| 2007/0260221 A1 | 11/2007 | Chesnin | |
| 2008/0097296 A1 * | 4/2008 | Pepin | A61M 25/0014 604/103 |

OTHER PUBLICATIONS

International Search Report from copending PCT Application No. PCT/US08/55715 mailed Aug. 15, 2008.
European Search Report from EP 14159757 dated Apr. 15, 2014.

* cited by examiner

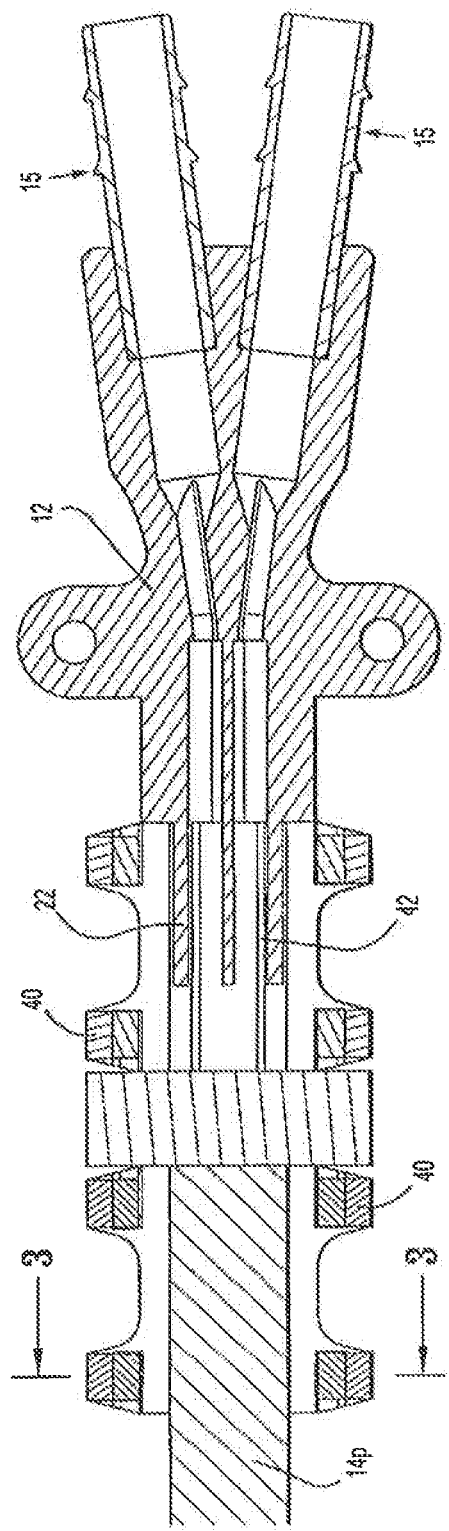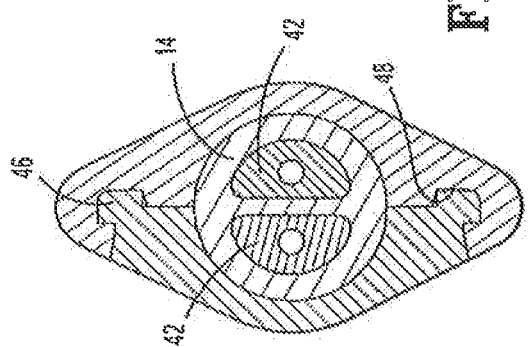
FIG. 2
FIG. 3

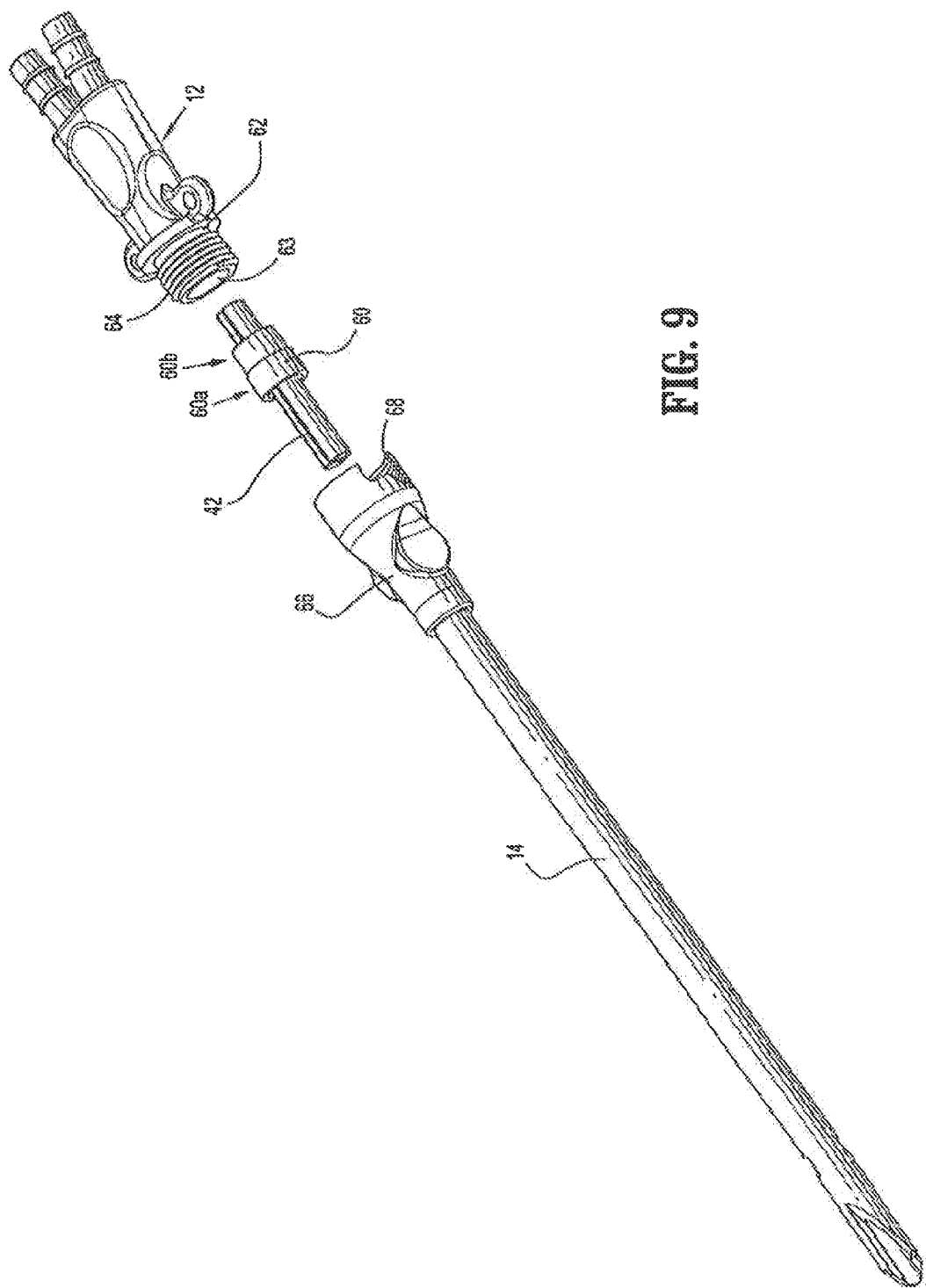

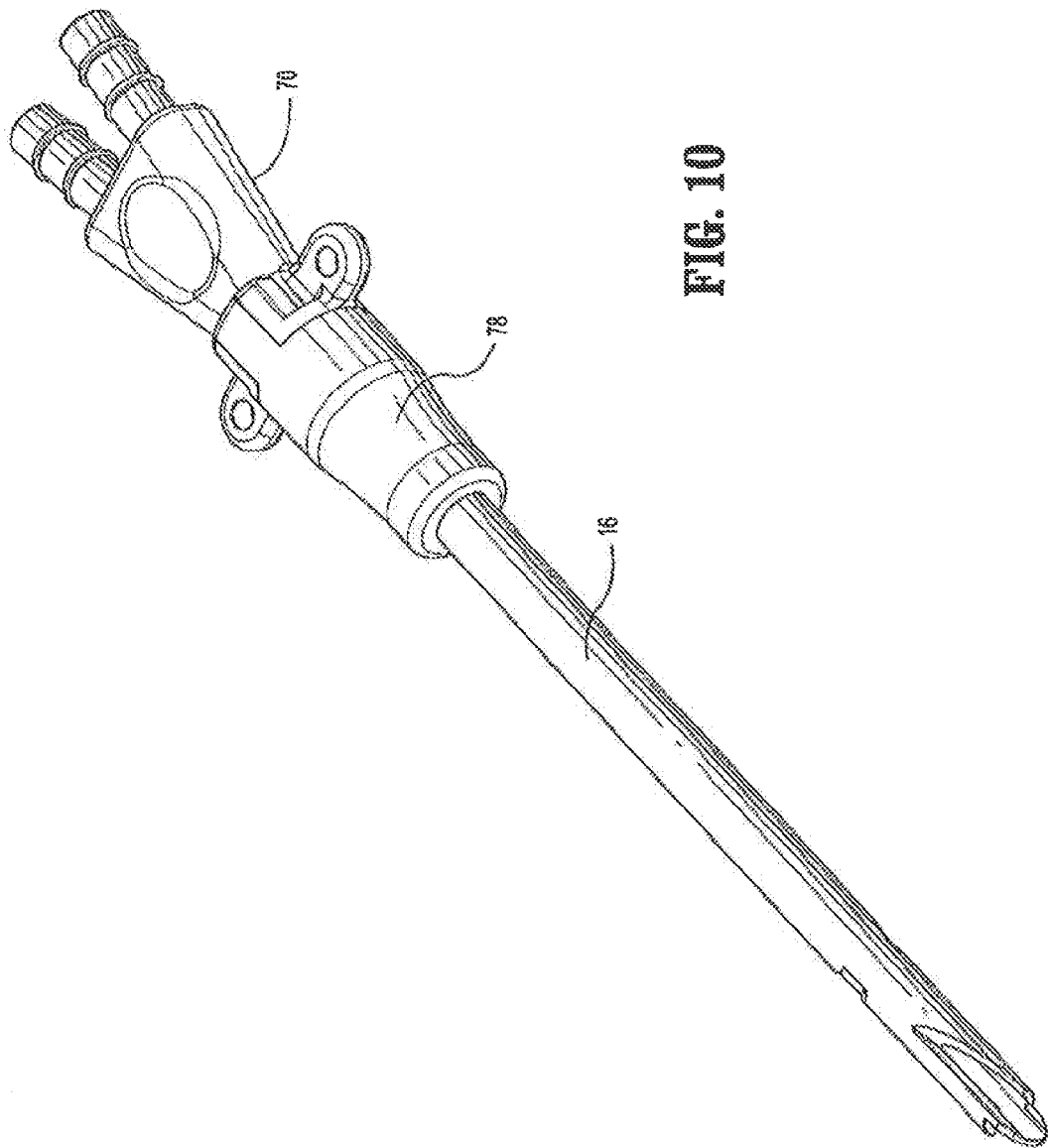

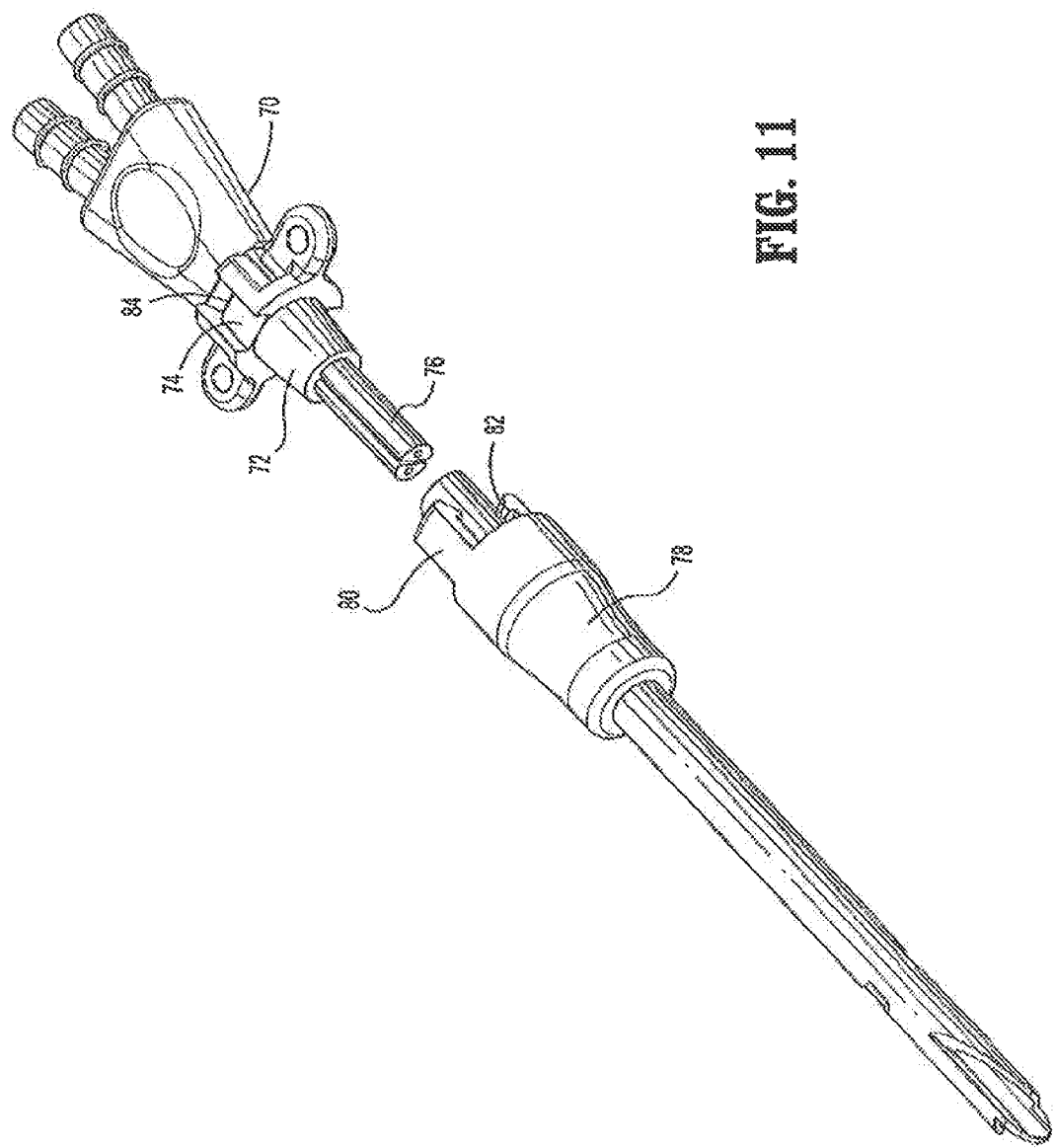

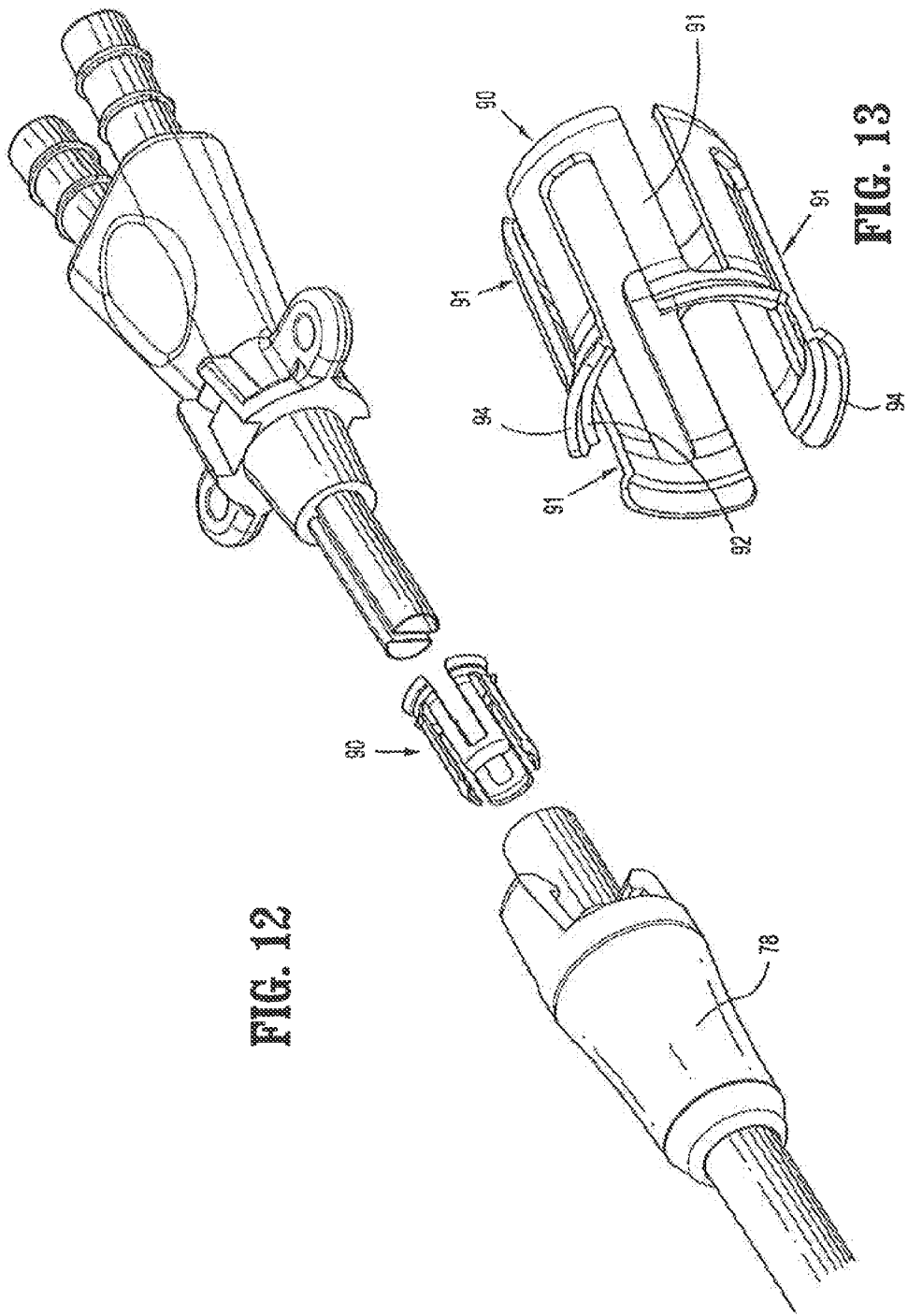

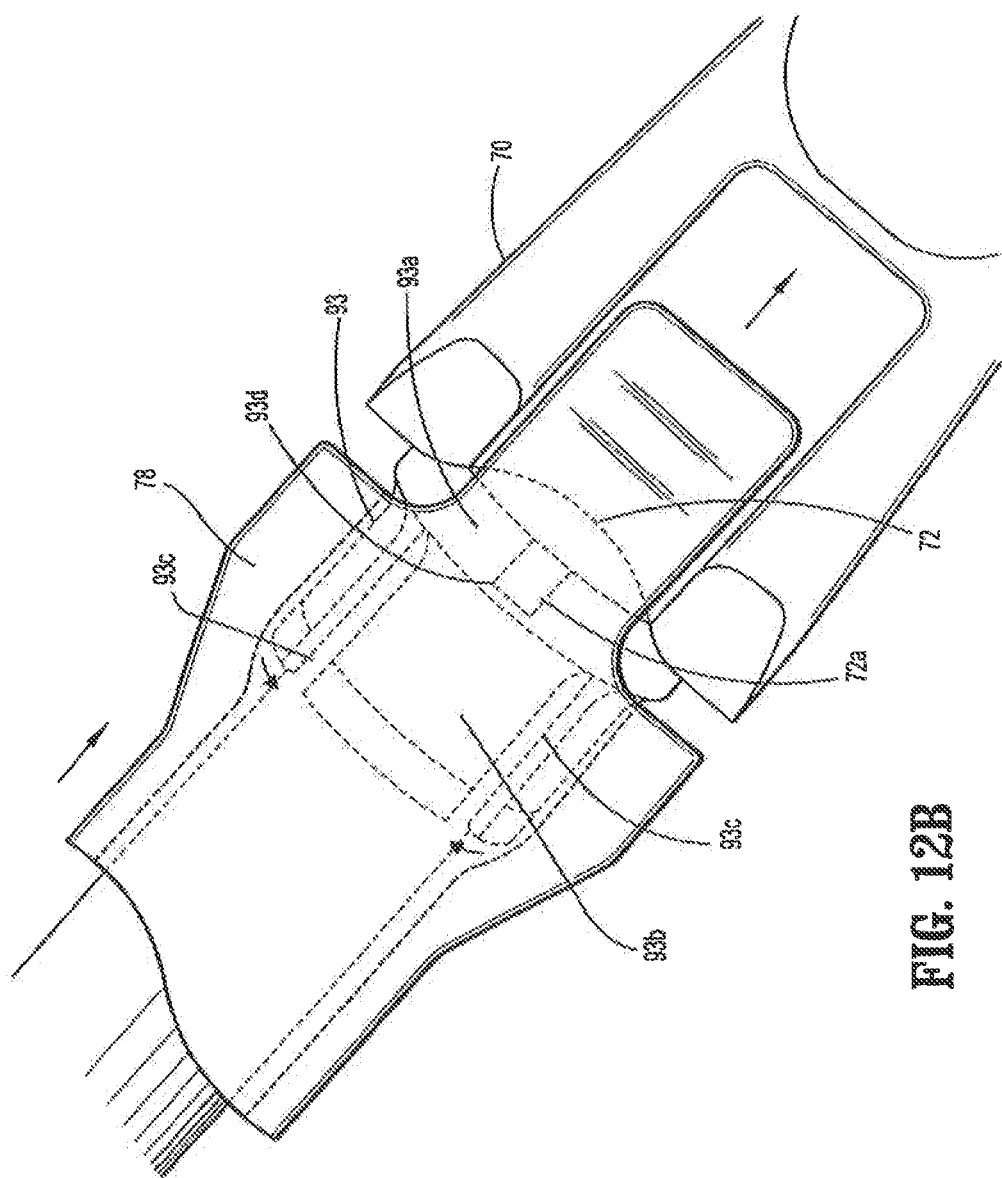

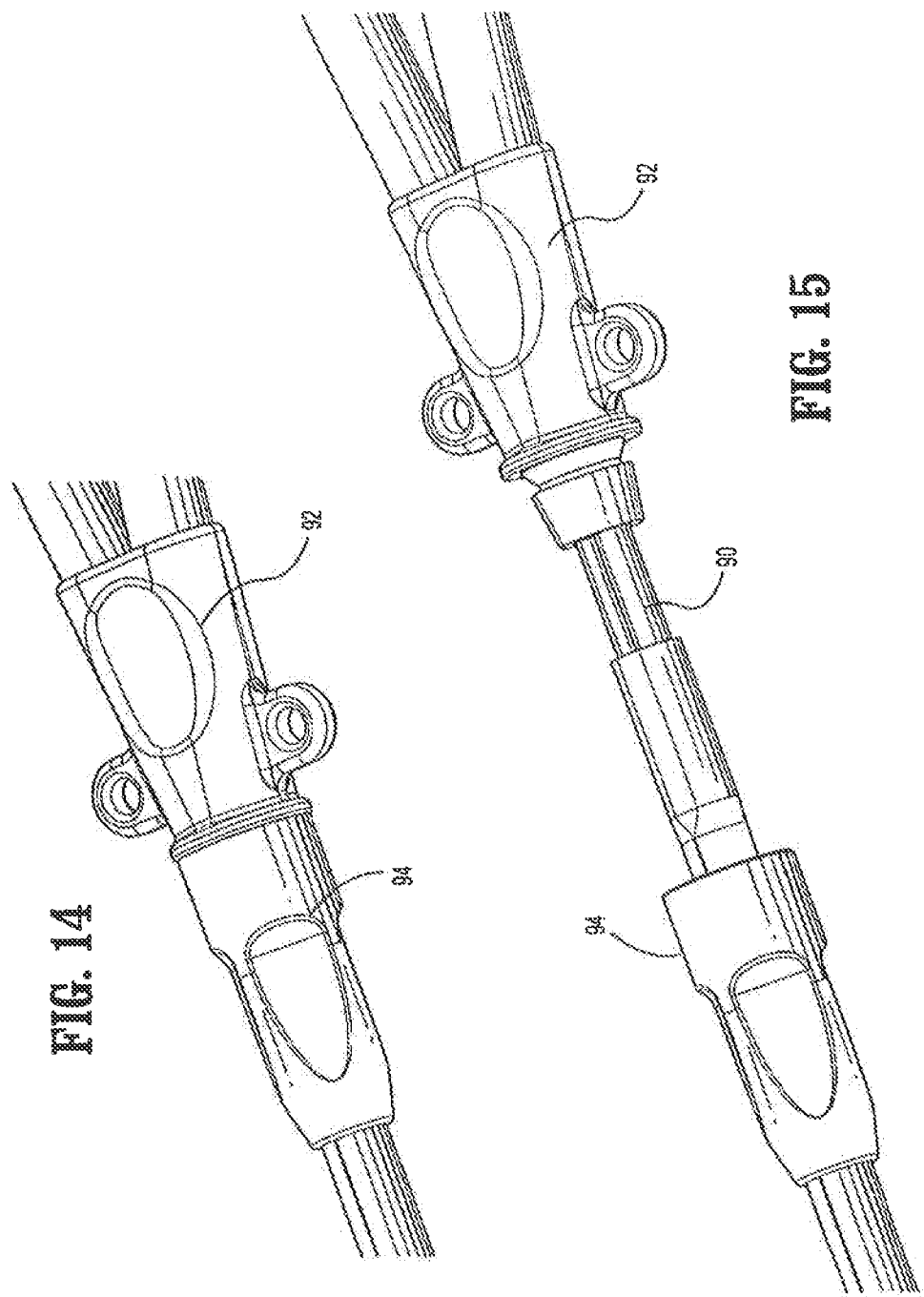

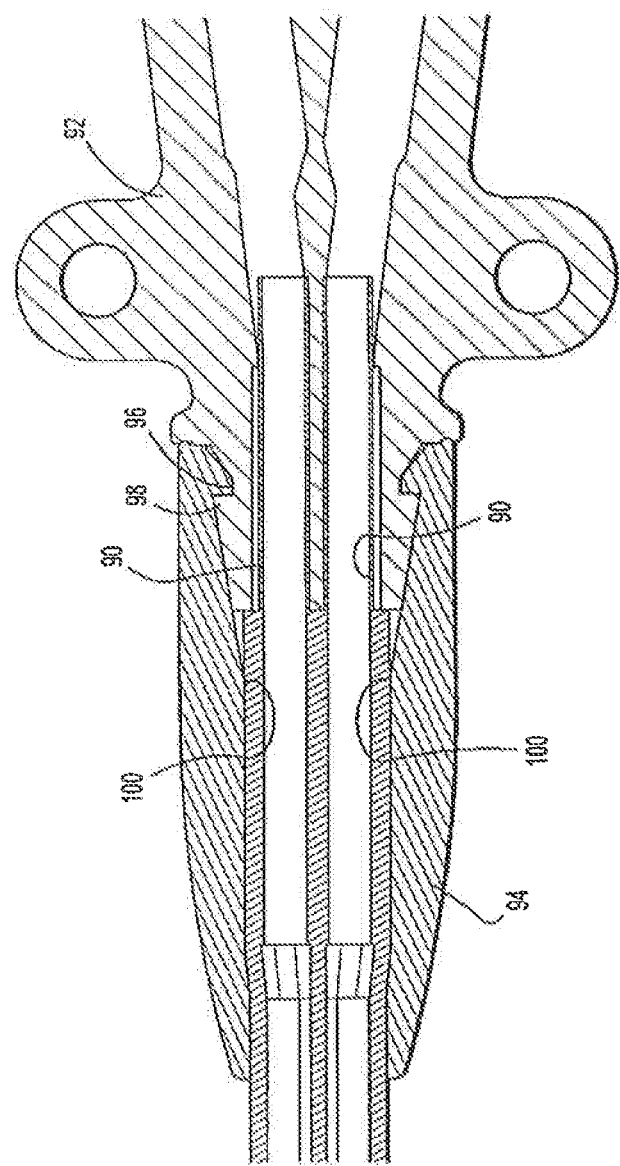

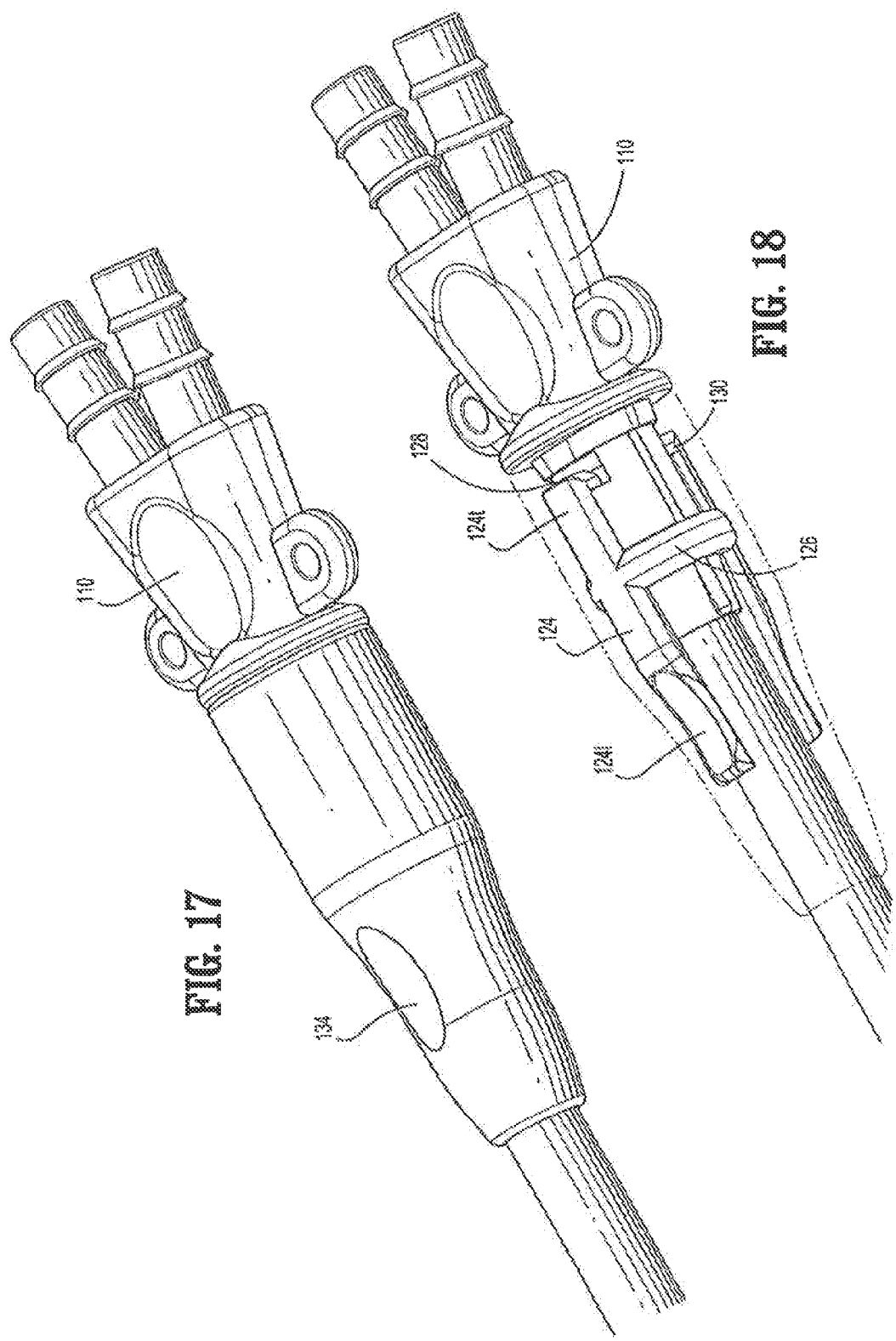

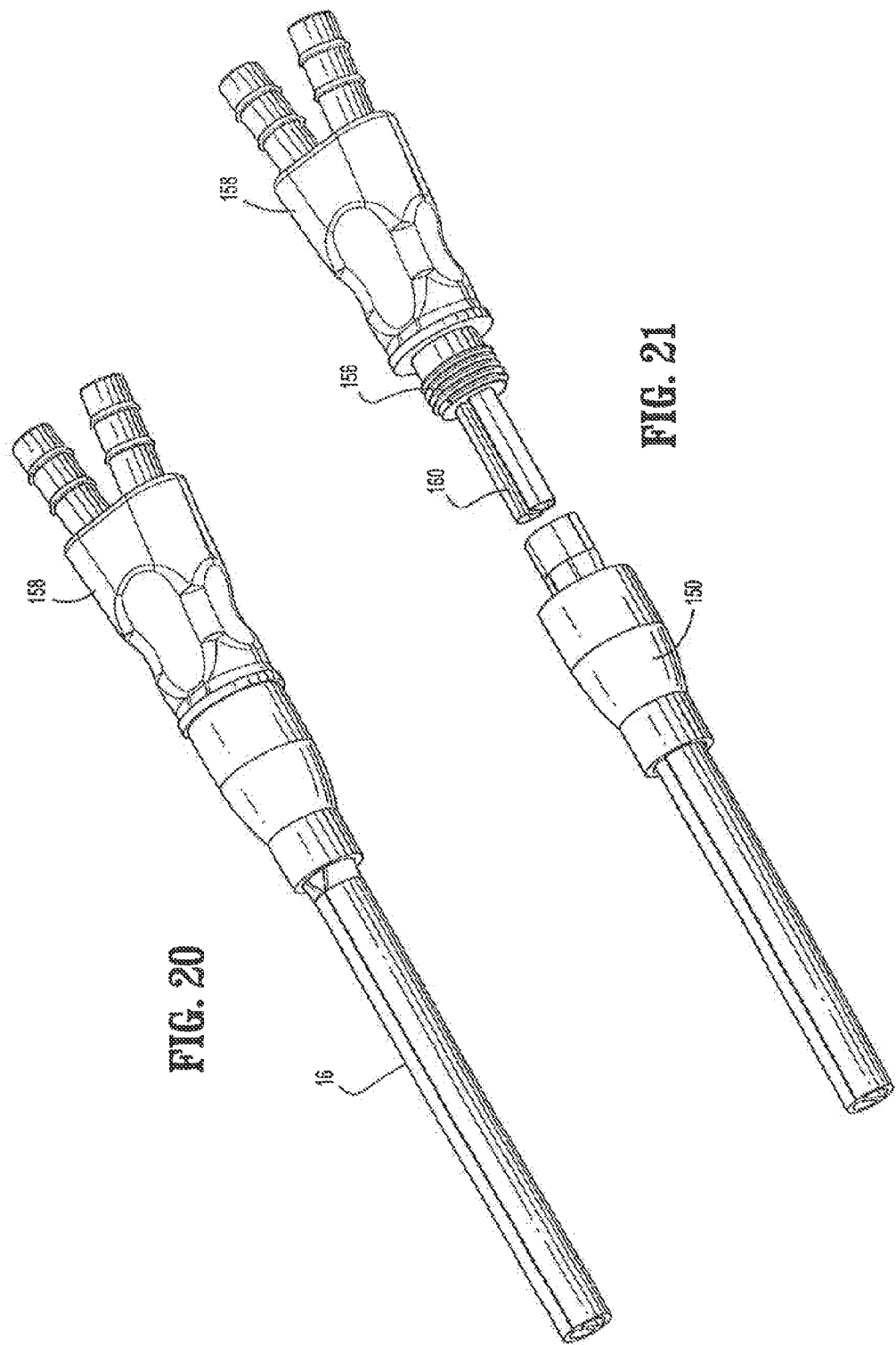

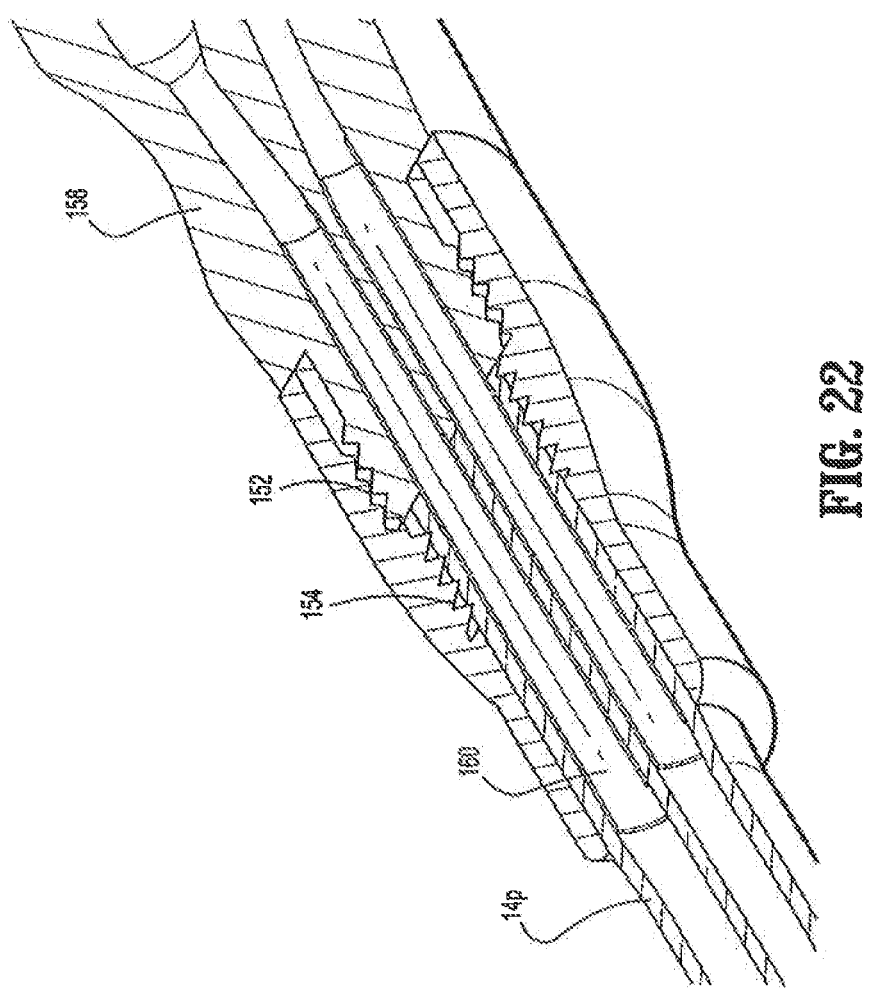

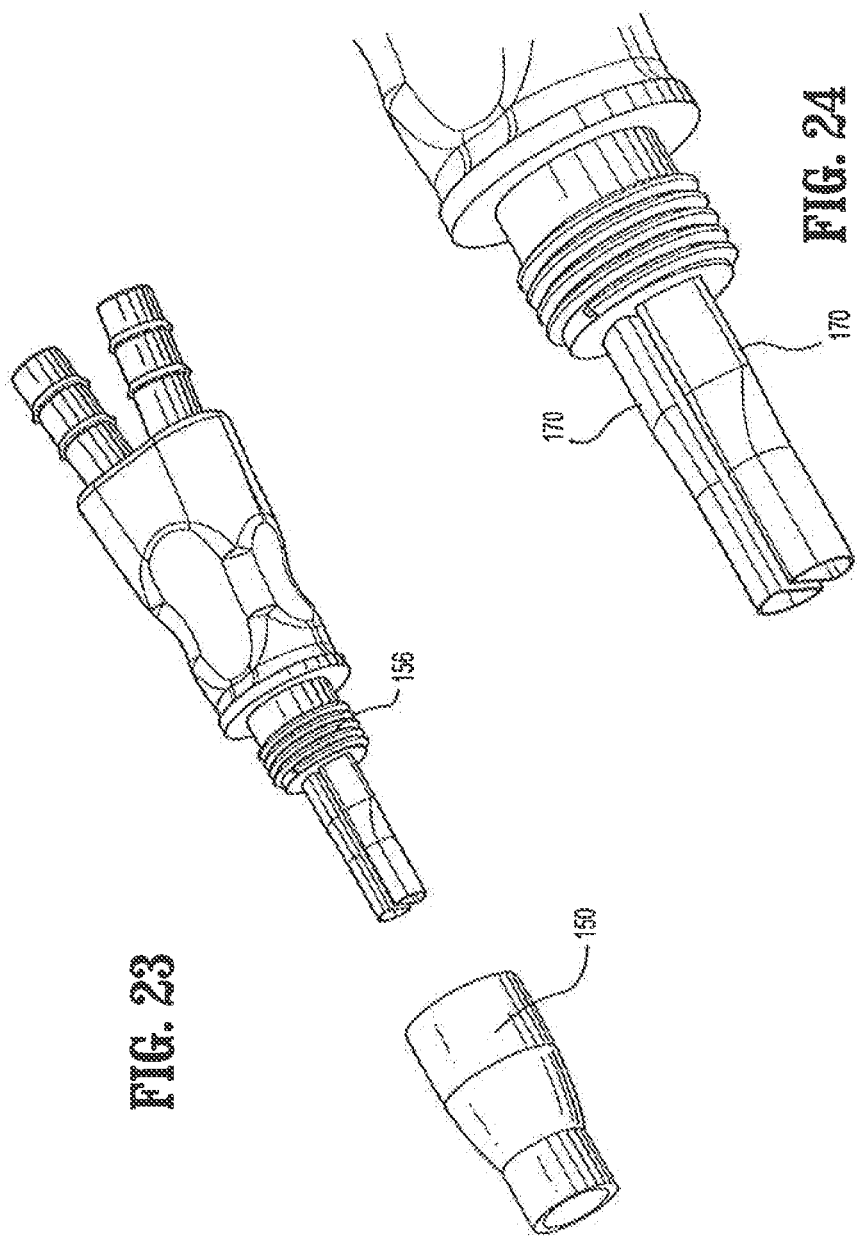

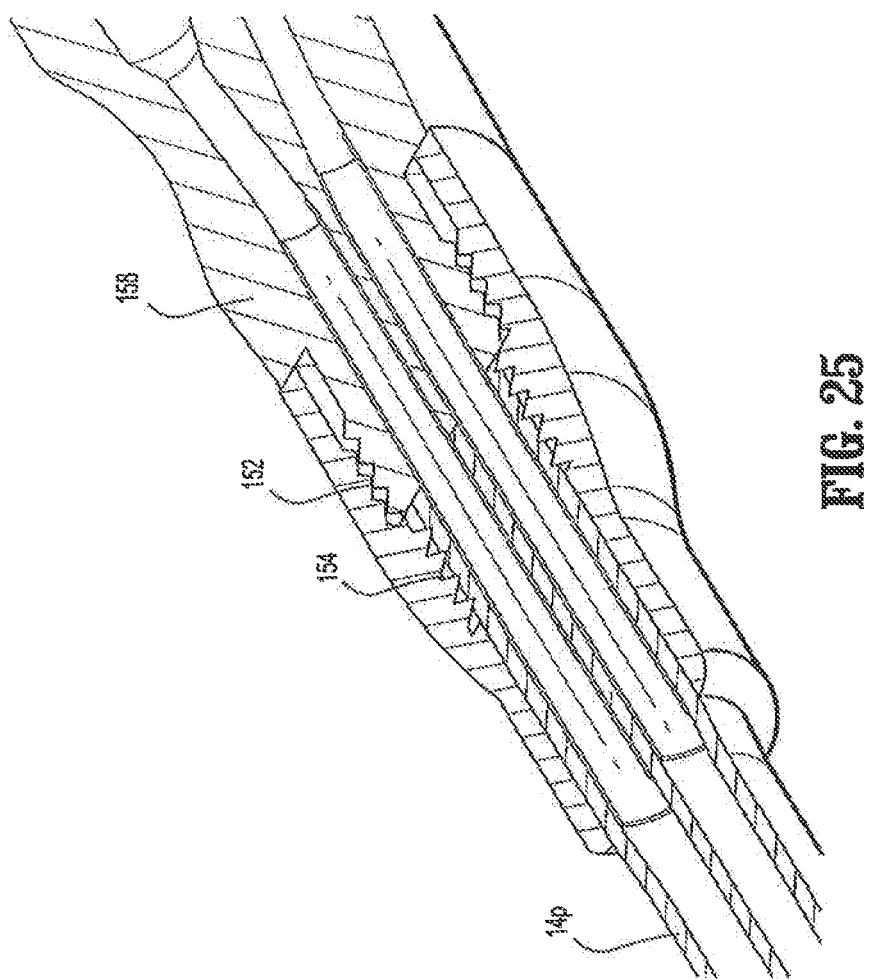

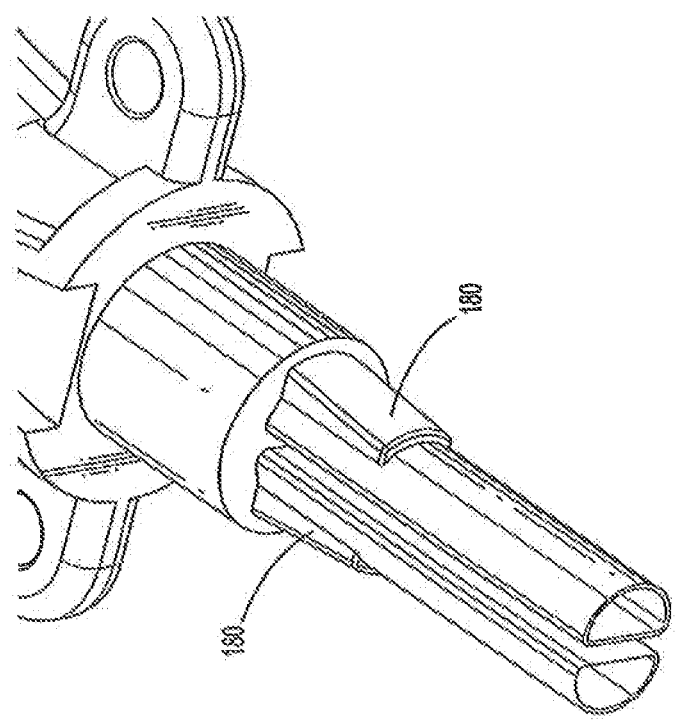

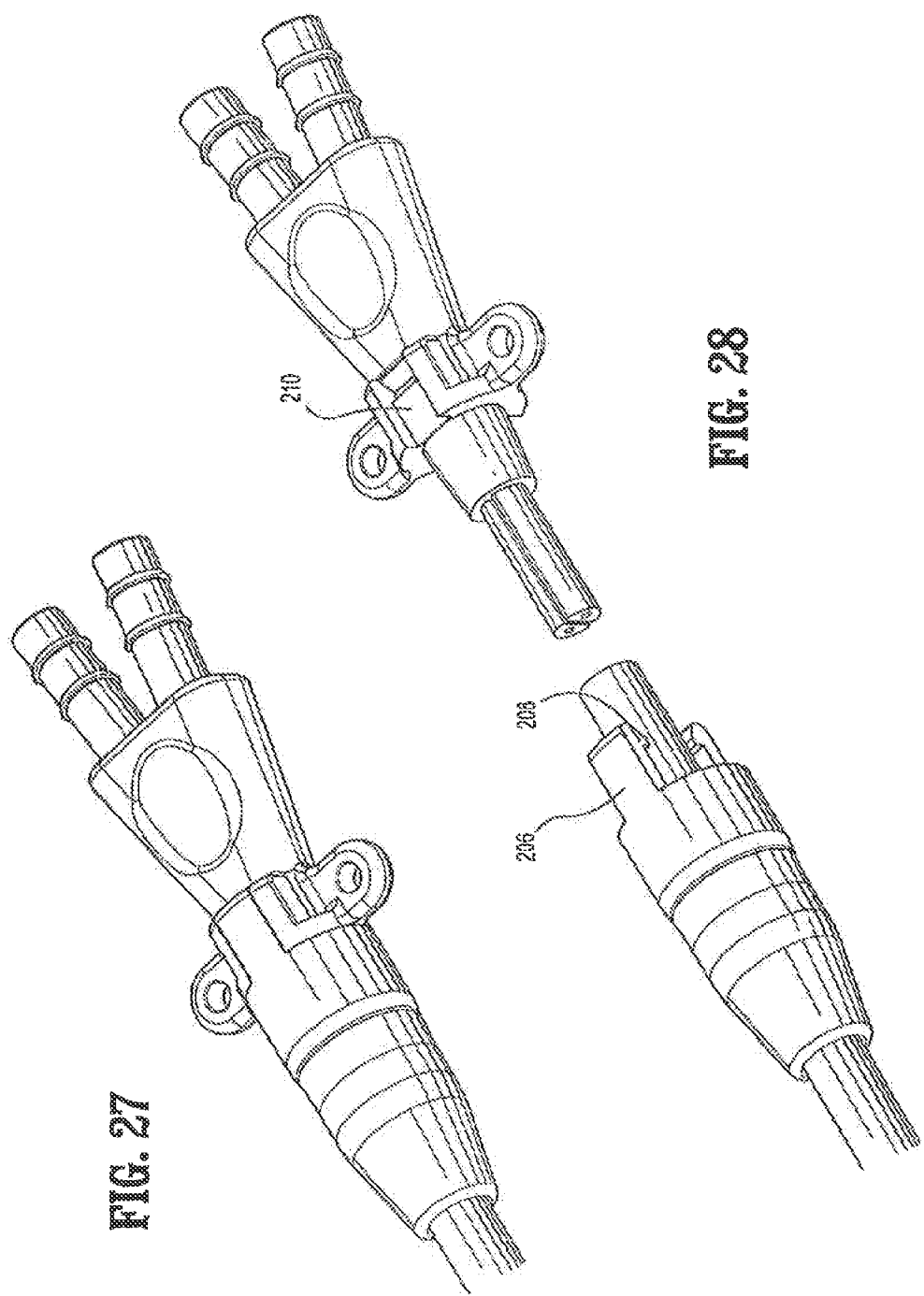

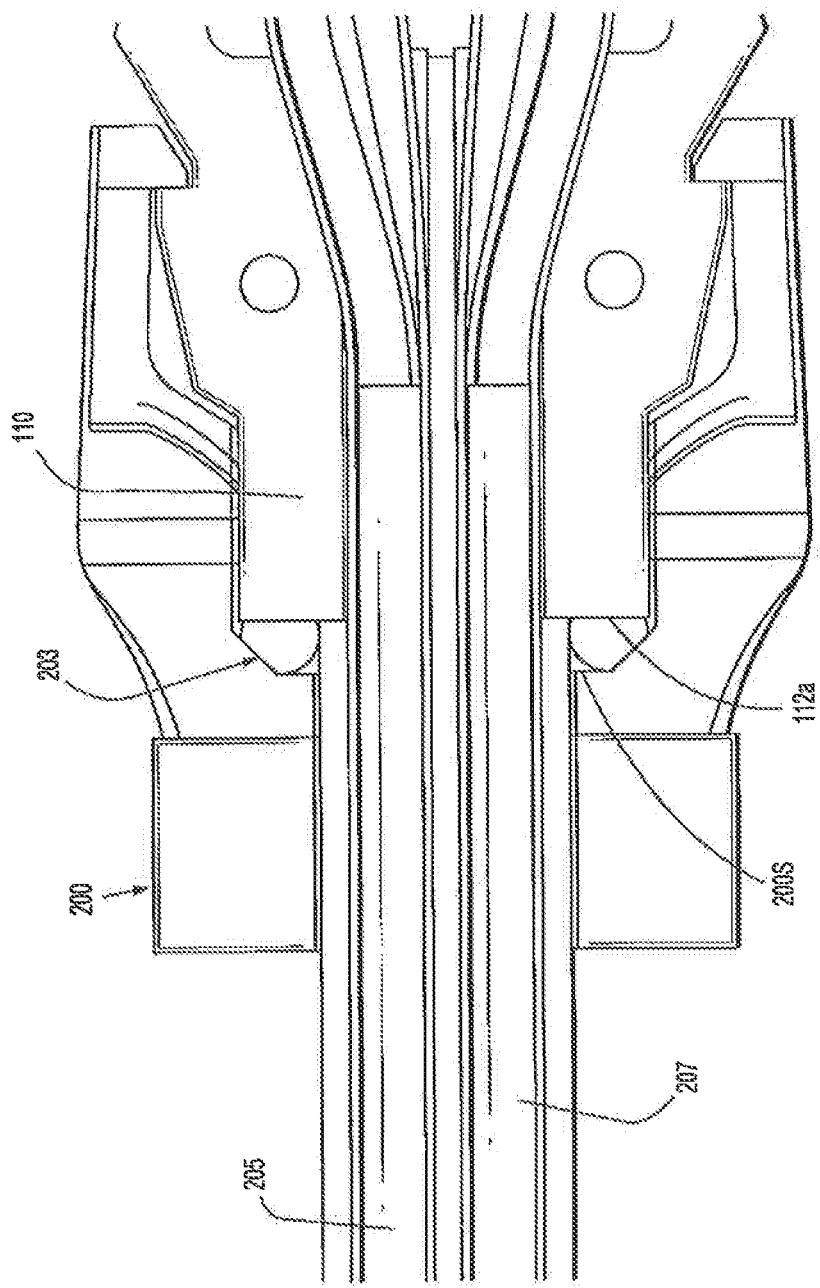

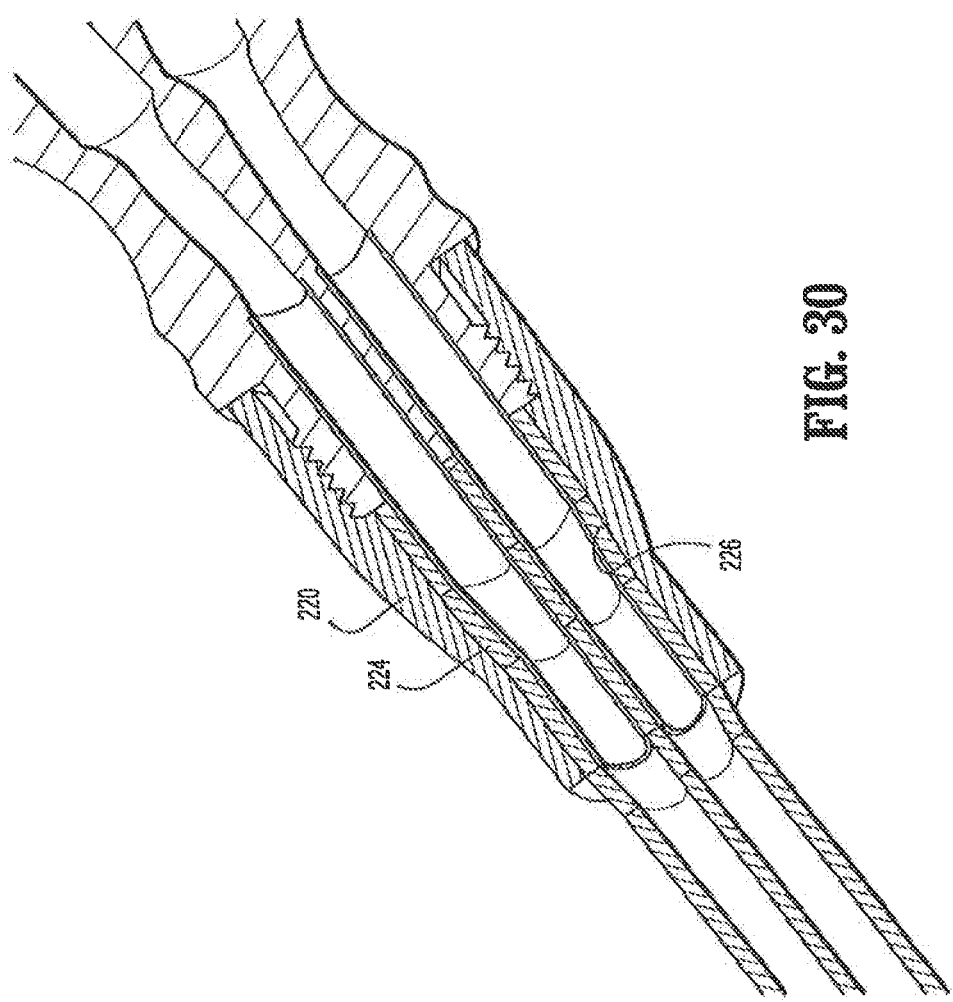

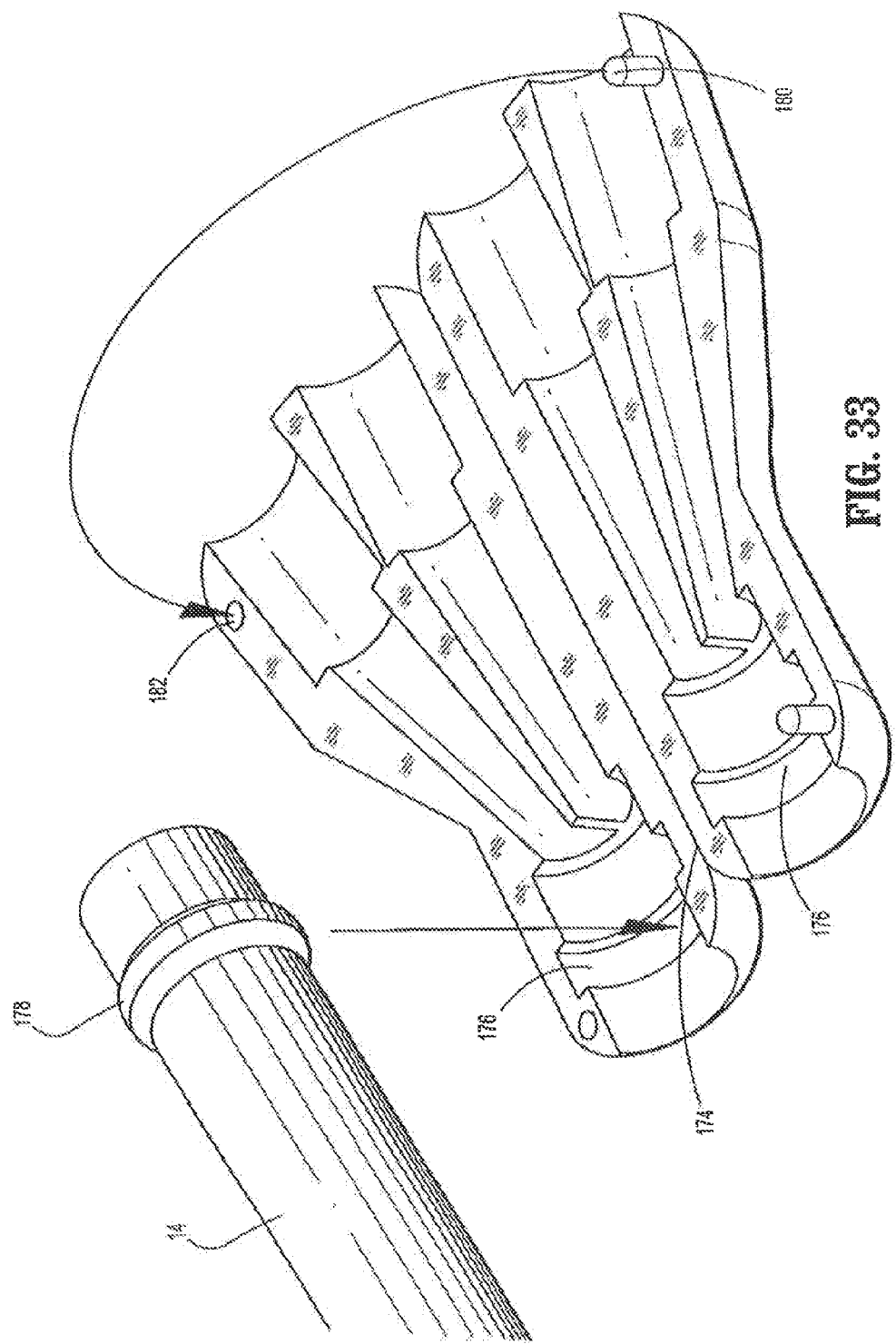

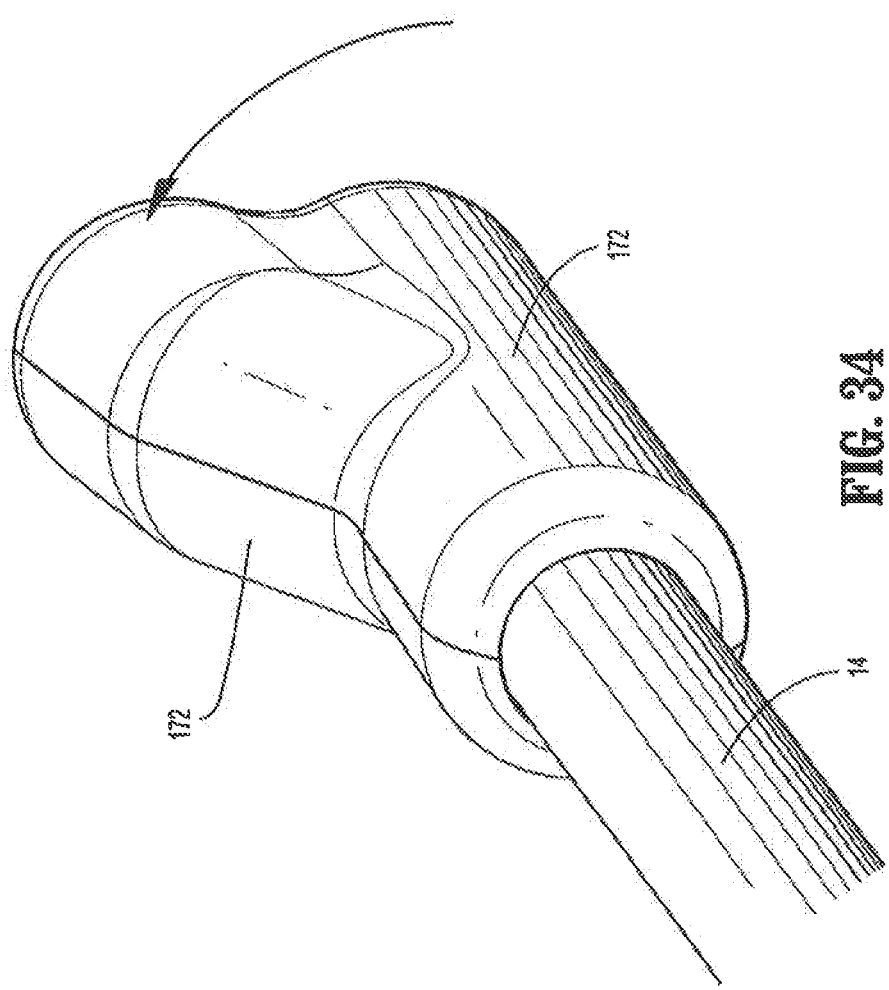

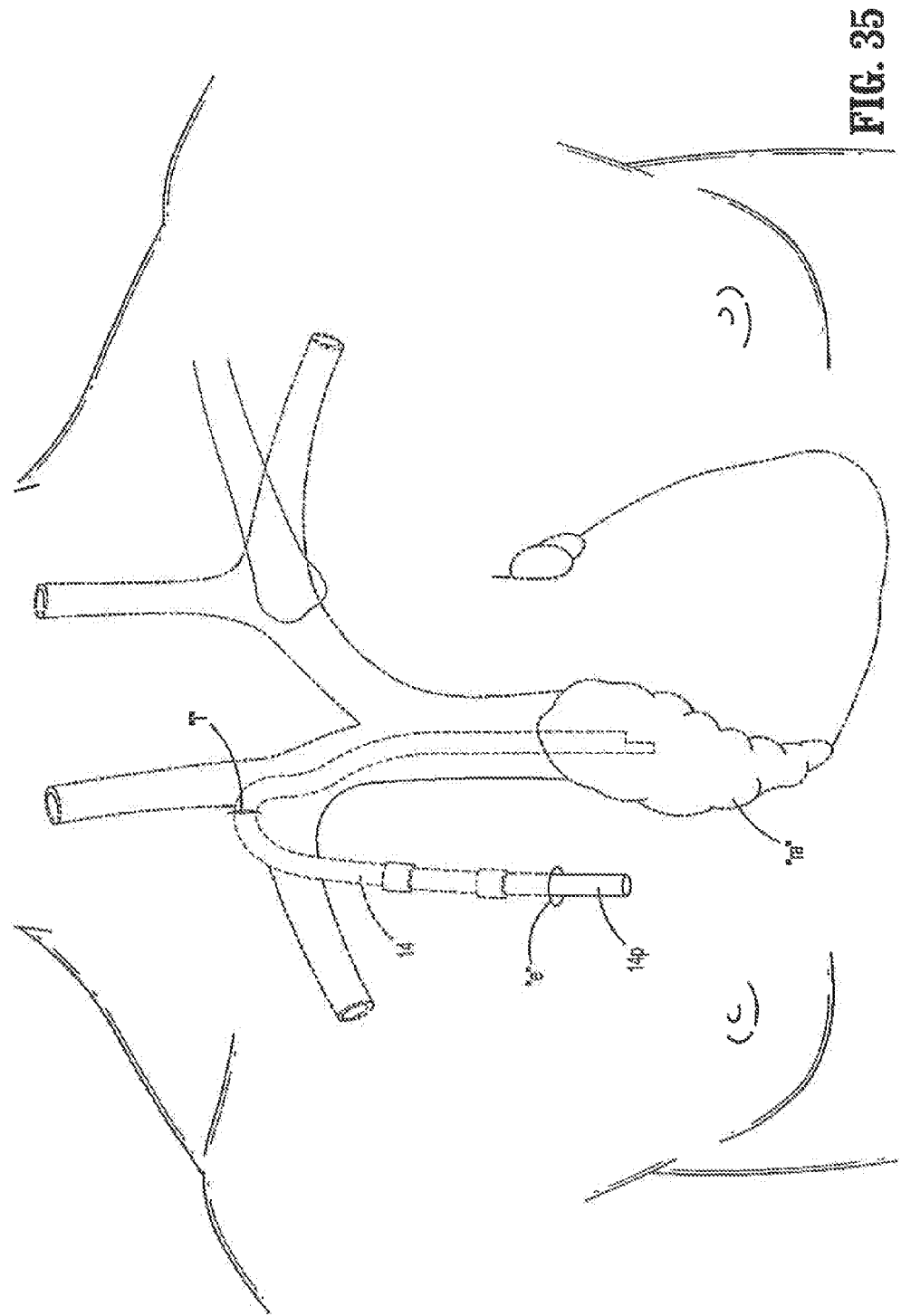

CATHETER SYSTEM WITH ATTACHABLE CATHETER HUB

CROSS REFERENCE TO RELATED APPLICATION(S)

The present application is a Continuation Application which claims the benefit of, and priority to, U.S. patent application Ser. No. 12/764,602, filed Apr. 21, 2010, which is a Divisional Application which claims the benefit of, and priority to, U.S. patent application Ser. No. 12/041,563, filed Mar. 3, 2008, now U.S. Pat. No. 7,731,708 issued Jun. 8, 2010, which claims the benefit of, and priority to, U.S. Provisional Patent Application Ser. No. 60/904,459, filed on Mar. 2, 2007, the entire contents of each of which are incorporated herein by reference.

BACKGROUND

1. Technical Field

The present disclosure is directed to a catheter assembly, and, in particular, relates to a catheter system adapted for use in a subcutaneous tunneling catheterization procedure. The present disclosure further relates to catheter hubs or housing mechanisms which are selectively attachable to an elongated catheter tube either prior, to or subsequent to, implantation of the catheter tube during a hemodialysis procedure.

2. Description of the Related Art

Catheters are flexible medical instruments intended for the withdrawal and introduction of fluids relative to body cavities, ducts, and vessels. Catheter instrumentation may have particular application in a hemodialysis procedure where blood is withdrawn from a blood vessel for treatment, and subsequently returned to the blood vessel for circulation. Known hemodialysis catheters include multiple lumens, such as dual lumen or triple-lumen catheters, permitting bi-directional fluid flow within the catheter whereby one lumen is dedicated for withdrawal of blood and the other lumen is dedicated for returning the treated blood to the vessel. During an exemplary hemodialysis procedure, a multiple lumen catheter is inserted into a body and blood is withdrawn through an arterial lumen of the catheter. The removed blood is directed to a hemodialysis unit which dialyzes, or purifies, the blood to remove waste, and toxins. The dialyzed blood is returned to the patient through a venous lumen of the catheter.

Various techniques are employed for the insertion of hemodialysis catheters including, e.g., with the use of guidewires, introduction stylets or the like. Some of these known techniques include subcutaneous tunneling methodologies where a subcutaneous tunnel is formed between two spaced openings in the skin with the use of a trocar or the like. One catheter end is introduced through an entry site or venotomy site for routing into, e.g., the jugular vein and routed to the heart. The trailing or proximal end is advanced through the subcutaneous tissue to exit a second exit opening adjacent the sternum of the patient beneath the venotomy site. Once the proximal end of the catheter is exposed, a catheter hub with extension tubes is fluidly connected to the catheter. One subcutaneous technique is disclosed in U.S. Pat. No. 5,509,897 to Twardowski et al., the contents of which is incorporated herein by its entirety.

SUMMARY

Accordingly, the present disclosure is directed to a hemodialysis catheter assembly adapted for use in a subcutaneous tunneling procedure. Various embodiments of the hemodialysis catheter assembly are disclosed. Each embodiment of the catheter assembly incorporates a mechanism for securing the catheter hub member to the elongated catheter, and to provide the requisite fluid communication between fluid passages within the hub and the catheter lumens within the catheter. The catheter hub member may be connected to the elongated catheter after implantation of the catheter via a subcutaneous tunneling procedure.

BRIEF DESCRIPTION OF THE DRAWINGS

Preferred embodiments of the disclosure will be better understood with reference to the accompanying drawings wherein:

FIG. 2 is a cross-sectional view taken along the lines 2-2 of FIG. 1;

FIG. 3 is a cross-sectional view taken along the lines 3-3 of FIG. 2;

FIG. 9 is a perspective view with parts separated illustrating the components of the catheter system of FIG. 8;

FIG. 10 is a perspective view an alternate embodiment of the catheter system;

FIG. 11 is a perspective view with parts separated illustrating the components of the catheter system of FIG. 10;

FIG. 12 is a perspective view with parts separated of an alternate embodiment of the catheter system of FIG. 10 incorporating a metal locking ring;

FIG. 12B is a perspective view of an alternate embodiment of the catheter system of FIG. 12;

FIG. 13 is a perspective view of the metal locking ring of FIG. 12;

FIG. 14 is a perspective view of an alternate embodiment of the catheter system illustrating the catheter hub;

FIG. 15 is a perspective view with parts separated of the catheter system of FIG. 14;

FIG. 16 is a side cross-sectional view of the catheter hub of FIGS. 14-15;

FIG. 17 is a perspective view of another alternate embodiment of the catheter system;

FIG. 18 is a view similar to the view of FIG. 17 with portions cut away to illustrate the internal components of the catheter system;

FIG. 20 is a perspective view of another alternate embodiment of the catheter system;

FIG. 21 is a perspective view with parts separated of the catheter system of FIG. 20;

FIG. 22 is a side cross-sectional view of the catheter hub of the catheter system of FIGS. 20-21;

FIG. 23 is a perspective view with parts separated of a catheter hub of another embodiment of the catheter system;

FIG. 24 is an enlarged perspective view of the connector tubes and threaded collar of the catheter hub of FIG. 23;

FIG. 25 is a side cross-sectional view of the catheter hub of FIG. 23 illustrating the securing of the catheter member;

FIG. 26 is a view of an alternate embodiment of the catheter hub of FIG. 23;

FIG. 27 is a perspective view of another alternate embodiment of the catheter system;

FIG. 28 is a perspective view with parts separated of the catheter system of FIG. 27;

FIG. 29A is a side cross-sectional view of an alternate embodiment of the catheter system;

FIG. 30 is a side cross-sectional view of a catheter hub of another embodiment of the catheter system.

FIG. 33 is a perspective view illustrating the interior of the catheter hub with a catheter member; and FIG. 34 is a view illustrating closing of the catheter hub about the catheter; and FIG. 35 is a view of a subcutaneous procedure in which the catheters systems may be used.

DETAILED DESCRIPTION OF THE EMBODIMENTS

Figure 1:
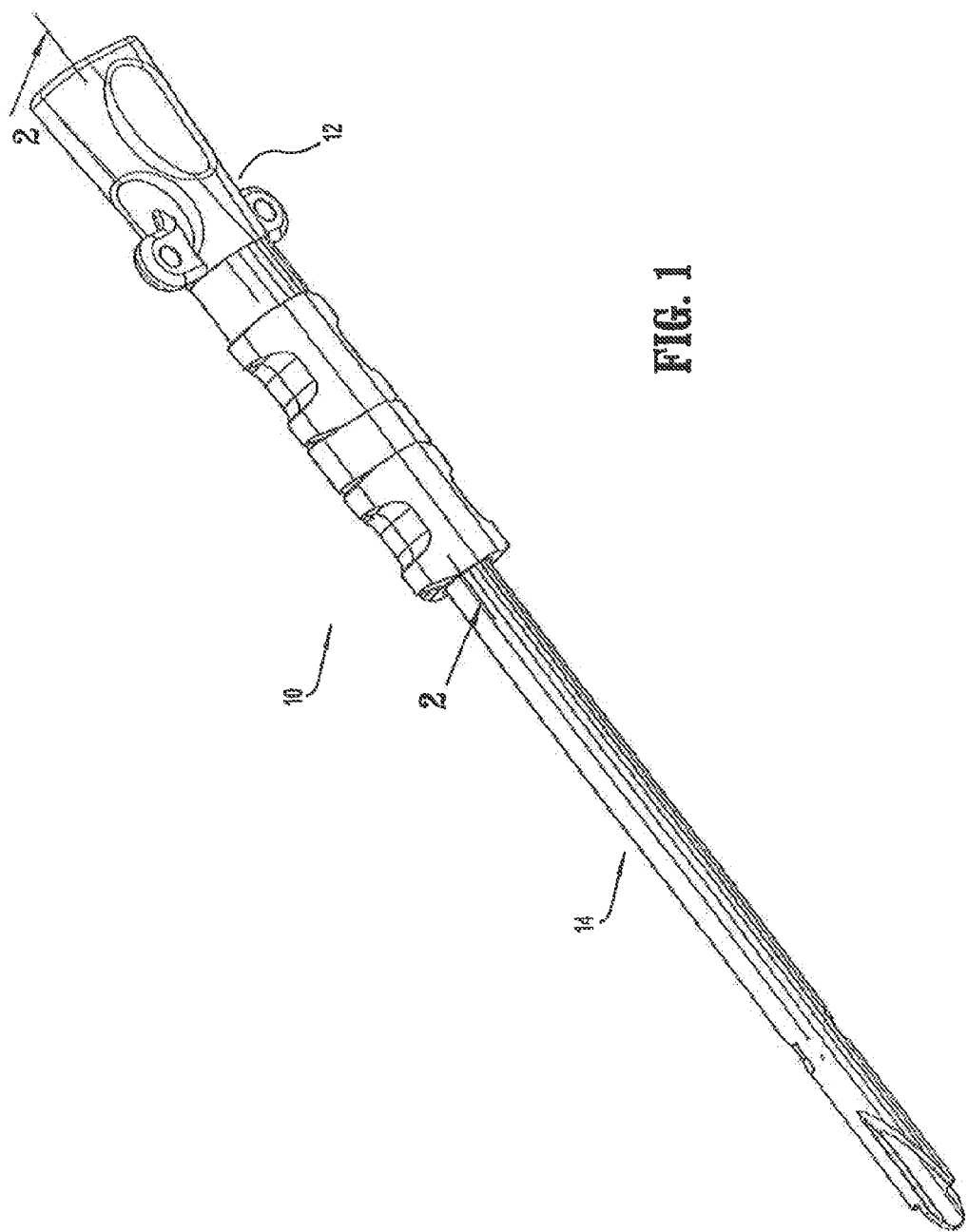
FIG. 1 is a perspective view of the catheter system in accordance with the principles of the present disclosure illustrating the attachable catheter hub and the elongate catheter member.
Figure 4:
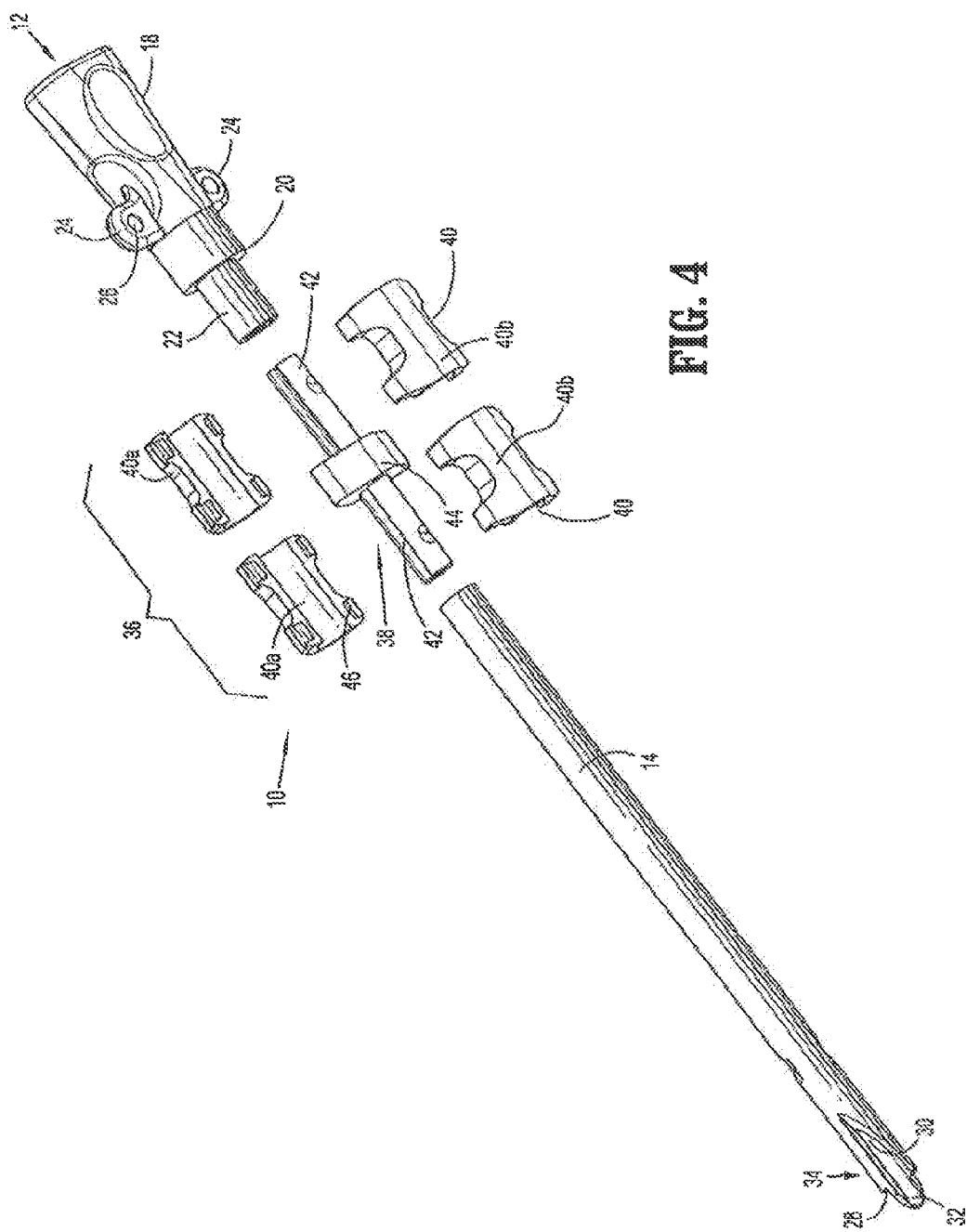
FIG. 4 is a perspective view with parts separated illustrating the components of the catheter system of FIG. 1.

The exemplary embodiments of the catheter systems and methods of use disclosed are discussed in terms of medical catheters for the administration of fluids (withdrawal or introduction) relative to the body of a subject and, more particularly, in terms of a hemodialysis catheter. However, it is envisioned that the present disclosure may be employed with a range of catheter applications including surgical, diagnostic and related treatments of diseases and body ailments of a subject. It is further envisioned that the principles relating to the catheter disclosed include employment with various catheter related procedures, such as, for example, hemodialysis, cardiac, abdominal, urinary, intestinal, and in chronic and acute applications. Moreover, the catheter can be used for administration of fluids such as, for example, medication, saline, bodily fluids, blood and urine.

In the discussion that follows, the term "proximal" or "trailing" will refer to the portion of a structure that is closer to a clinician, while the term "distal" or "leading" will refer to the portion that is further from the clinician. As used herein, the term "subject" refers to a human patient or other animal. The term "clinician" refers to a doctor, nurse or other care provider and may include support personnel.

The following discussion includes a description of the catheter system, followed by a description of an exemplary method of operating the catheter in accordance with the principles of the present disclosure. For discussion purposes, the catheter will be discussed in terms of a hemodialysis catheter and the method of operation will be discussed in terms of a reverse tunneling procedure utilized for positioning the catheter during a dialysis procedure. However, those skilled in the art will appreciate the catheter has many other applications in addition to dialysis applications.

Referring now to the FIGURES wherein like components are designated by like reference numerals throughout the several views, FIGS. 1-4 illustrate in perspective views, the hemodialysis catheter 10 in accordance with the principles of the system of the present disclosure. Catheter 10 includes several components assembled together, namely, catheter hub or housing 12 and elongated catheter tube or member 14 extending distally from the catheter hub 12. In general, catheter hub 12 is attachable to catheter member 14 subsequent to implantation of the catheter member 14 relative to the patient during a medical procedure such as, e.g., a hemodialysis procedure. Various mechanisms for attaching catheter hub 12 to catheter tube are contemplated by the present disclosure and will be described in greater detail hereinbelow.

Catheter hub 12 is advantageously dimensioned for engagement by the clinician. Catheter hub 12 includes proximal or trailing housing section 18 and distal or leading housing section 20 adjacent catheter members 14. Trailing housing section 18 is connectable to extension tubes (not shown) through extension tube mounts 15, which serve as the venous and arterial lines leading to the hemodialysis machine as is conventional. Leading housing section 20 defines an annular collar 22. Annular collar 22 has internal lumens 23 in fluid communication with fluid passages 25 extending through catheter hub 12. Internal lumens 23 may be generally D-shaped. Other configurations are also envisioned. Annular collar 22 may be formed of a compressible material. Catheter hub 12 may further include a pair of opposed suture wings 24 along its outer surface. Suture wings 24 define openings 26 dimensioned for receiving sutures which may be utilized in securing catheter hub 12 relative to the subject. In an alternative embodiment, catheter hub 12 may have an annular groove (not shown) in its outer wall in lieu of suture wings 24. A suture may be wrapped within annular groove and subsequently secured relative to the subject.

Catheter member 14 may be any catheter tube suitable for use with a desired medical procedure. Catheter member 14 may be single, dual or triple lumen catheters. In the embodiment shown in FIG. 1, catheter member 14 is a dual lumen catheter having particular application in a hemodialysis procedure. However, catheter member 14 may be any commercial available catheter member such as the catheter members sold under the trademarks Palindrome and Mahurkar. In this regard, catheter member 14 has first and second longitudinal lumens 28, 30 separated by a septum wall 32 which extends the length the catheter tube. Each of the first and second longitudinal lumens 28, 30 may define a D-shaped opening in cross-section. Other lumen arrangements are also envisioned including circular, pie shaped or other shapes known in the art. Coaxial lumens are also envisioned. Leading or distal end 34 of catheter member 14 may have various configurations. In one embodiment, the arrangement of catheter distal end 34 is similar to an embodiment disclosed in commonly assigned U.S. Patent Publication No. 2005/0267400 to Haarala et al., filed Feb. 11, 2005, the entire contents of which is incorporated herein by reference. Other arrangements, e.g., as disclosed as alternate embodiments in the Haarala '400 publication, are also envisioned.

Catheter member 14 is preferably flexible and may be formed by conventional injection molding or extrusion means. The wall of catheter member 14 may include reinforcing material if desired. Catheter member 14 may have a pre-curved configuration in its normal state, i.e., have a preformed bend which it normally assumes in the absence of an external stressor to conform to a body cavity or vessel in which the catheter member is to be positioned. Alternatively, catheter member 14 may be devoid of any normally curved orientation.

Referring still to FIGS. 1-4, hub attachment mechanism will be discussed. Hub attachment mechanism 36 includes multiple tube connector 38 and at least one, preferably, two locking collars 40. Multiple tube connector includes two connector tubes 42 and connector collar 44. Connector collar 44 includes two openings therethrough which accommodate connector tubes and maintains the connector tubes 42 in side by side but slightly spaced relation. Connector collar 44 may be secured to connector tubes 42 if desired. Connector tubes 42 each define a cross-section which generally approximates the cross-section of lumens of catheter member 14 and internal passages within catheter hub 12. In one embodiment, the cross-section of connector tube is generally D-shaped to at least correspond to the D-shaped arrangement of catheter member.

Locking collars 40 are each split into two substantially equal half rings 40a, 40b. Means for connecting half rings are envisioned. In one embodiment, one half ring 40a of locking collar 40 includes at least one locking projection 46 which is receivable in a corresponding recess(es) 48 of the opposed locking ring 40b in snap relation to secure the half rings together. Other means for securing half rings 40a,40b are also envisioned including with the use of cements, adhesives, tongue-groove arrangement or the like. Half rings 40a,40b of locking collars 40 may be connected together through a hinge or the like or connected by a tether.

Upon assembly of catheter hub 12 to catheter member 14 when, e.g., catheter member 14 is appropriately positioned relative to the body, connector tube assembly 38 is first positioned within catheter member 14 with catheter tube ends of the first and second tubes 42 being received within respective lumens of the catheter. Preferably, proximal end of catheter member 14 is advanced along catheter tube ends until the proximal face of catheter contacts connector collar 44. Similarly, hub tube ends of connector tubes 42 are positioned within internal passages of catheter hub 12 and the catheter hub 12 is advanced along the catheter tube ends. Thereafter, half rings 40a,40b of one locking collar 40 are positioned about proximal end 14p of catheter member 14 and the half rings 40a,40b of the second collar 40 are positioned about hub mounting collar 22 of catheter hub 14. Each of respective half rings 40a,40b is snapped together to the condition depicted in FIG. 1. In this position, locking collar 40 compresses proximal end 14p of catheter member 14 against catheter tube ends of connector tubes 42 and locking collar 40 compresses mounting collar 22 of catheter hub 12 against hub tube ends of connector tubes 42. With this arrangement, a compressive frictional relationship is established between locking collars 40 and respective proximal end 14p of catheter tube 14 and hub mounting collar 22 to thereby secure catheter member 14 and catheter hub 12 to connector assembly 38 and attaching catheter hub 12 to catheter member 14. It is also envisioned that half rings 40a, 40b of locking collars 40 may be integrally, or monolithically, formed as a single unit resembling a clam shell arrangement. Half rings 40a, 40b could fold along hinges to assume the locked position around catheter hub 12 and catheter member 14.

Figure 5:
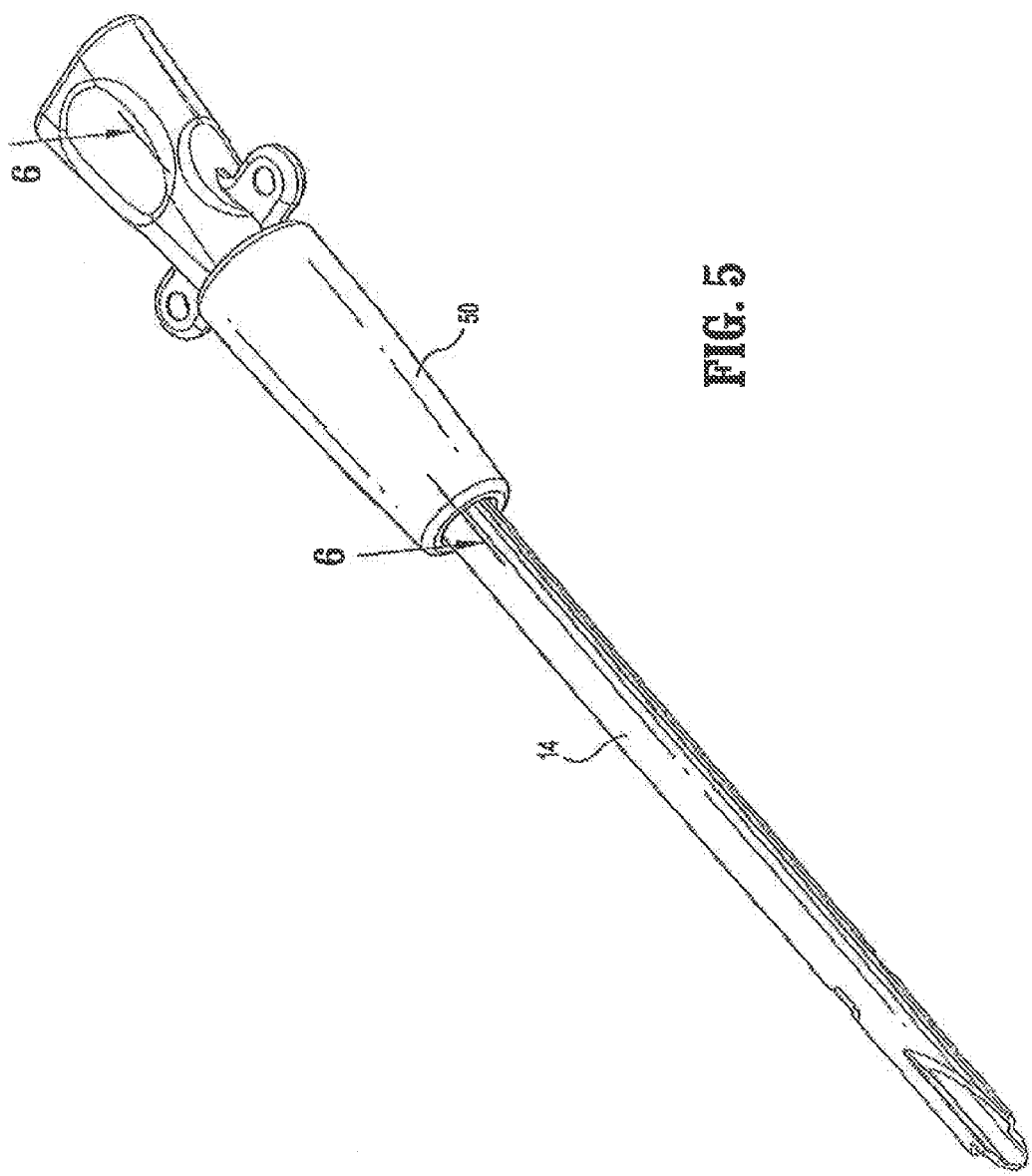
FIG. 5 is a perspective view an alternate embodiment of the catheter system.
Figure 6:
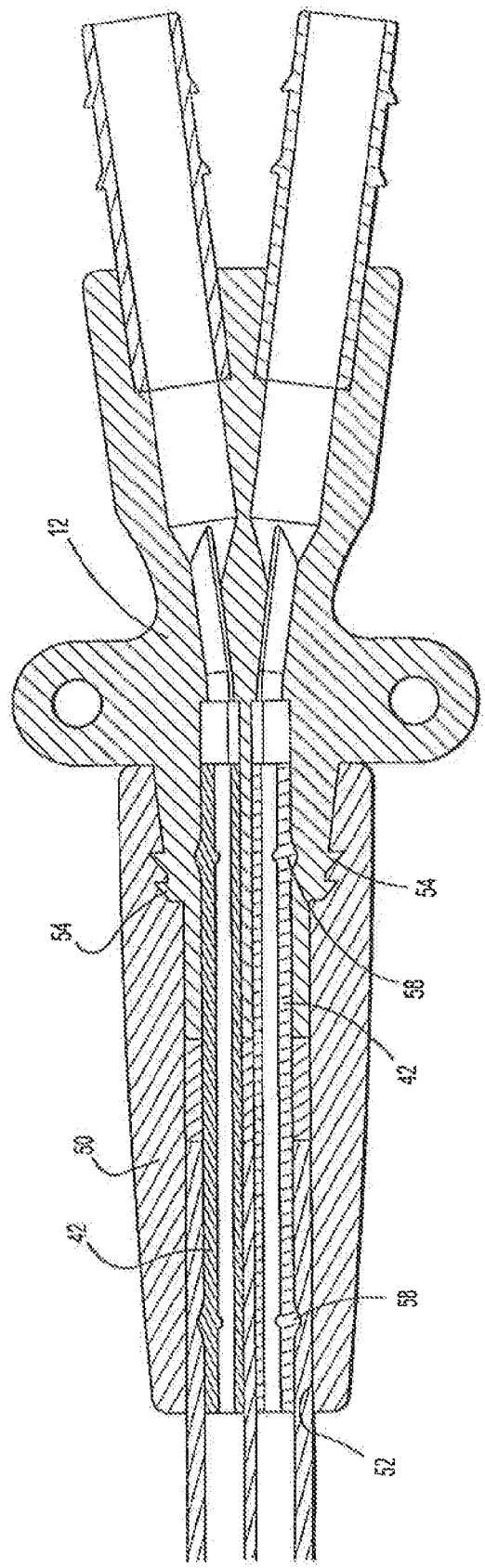
FIG. 6 is a cross-sectional view taken along the lines 6-6 of FIG. 5.
Figure 7:
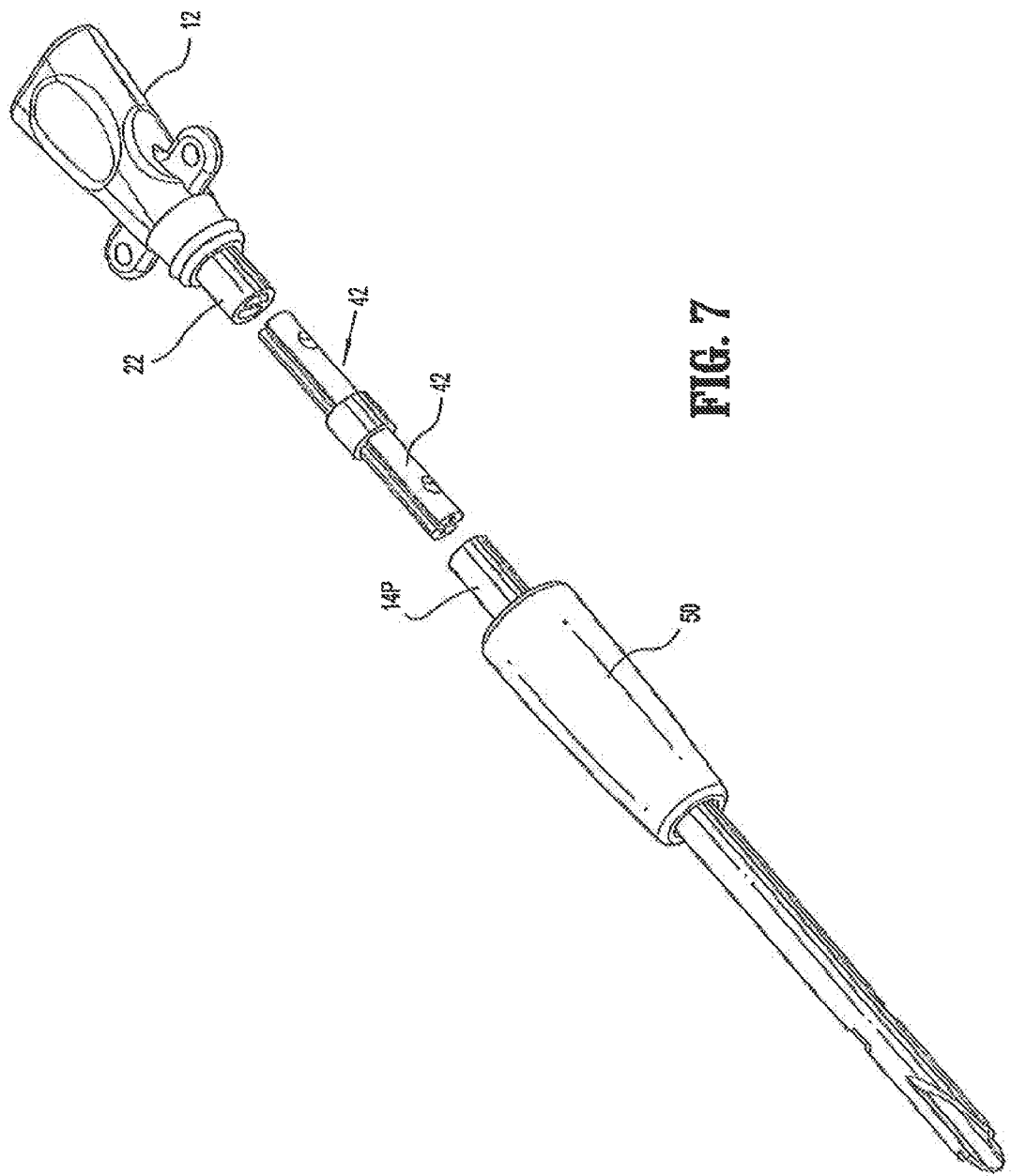
FIG. 7 is a perspective view with parts separated illustrating the components of the catheter system of FIG. 5.

FIGS. 5-7 illustrate an alternate embodiment of the hub attachment mechanism of FIGS. 1-4. In accordance with this embodiment, locking collars are replaced with single elongate locking sleeve which is coaxially positionable about the proximal end of catheter member. Connector assembly is similar to the connector assembly of FIGS. 1-4, with connector tubes being positioned within lumens of catheter member and passages of catheter hub 12 in the manner discussed hereinabove. Locking sleeve 50 is fabricated from a suitable elastomeric material such that it may stretch when positioned over the proximal end 14p of catheter member 14 and hub mounting collar 22 of catheter hub 12. Locking sleeve 50 is advanced in a proximal direction toward catheter hub 12 which causes internal surfaces 52 of locking sleeve 50 to compress the proximal end 14p of catheter member 14 against connector tube end in frictional relation therewith. In one embodiment, the internal bore of locking sleeve 50 is less in dimension or diameter than the cross-sectional dimension of connector ends of connector tubes 42 requiring the locking sleeve 50 to stretch over the connector tubes 42. The proximal end of locking sleeve 50 is continually advance toward catheter hub 12 to be positioned about peripheral ribs 54 of the catheter hub 12. Peripheral ribs 54 also serve to secure locking sleeve 50 to catheter hub 12. As best depicted in FIG. 6, locking sleeve 50 may compress the proximal end 14p of catheter member 14 tube and/or hub mounting collar 22 to secure connector tubes 42, catheter member 14 and catheter hub 12. Connector tubes 42 may also possess raised protrusions 58 on its outer surface on both connector end and hub end of the tubes 42 to facilitate the frictional relationship between the components. The elastomeric characteristics of locking collar 50 may facilitate the establishment of a seal about the catheter member.

Figure 8:
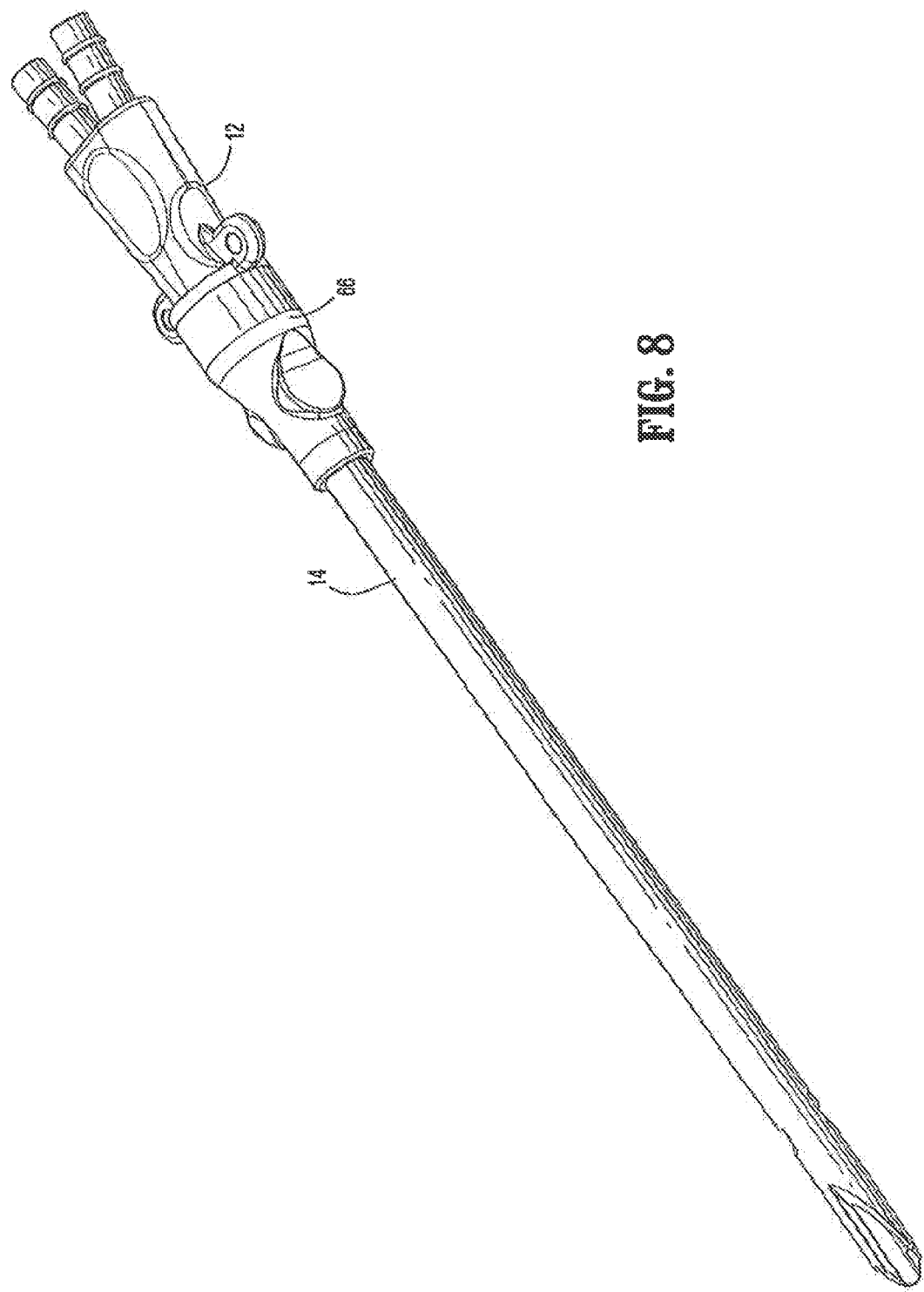
FIG. 8 is a perspective view an alternate embodiment of the catheter system.

FIGS. 8-9 illustrates another embodiment of catheter system. In accordance with this embodiment, an elastomeric grommet 60 is mounted or molded about connector tubes 42. The elastomeric grommet 60 includes first collar segment 60a and second collar segment 60b. First collar segment 60a defines a cross-sectional dimension that is greater than the cross-sectional dimension of second collar segment 60b. Connector tubes 42 are positioned within the catheter hub 12 and catheter member 14 is mounted about the connector tubes 42 and advanced to the collar or grommet 60. Catheter hub 12 includes mounting collar 62 having an external threaded portion 64. Collar segment 60b of the elastomeric grommet 60 is dimensioned for reception within an internal bore 63 of mounting collar 62. Second collar segment 60b engages the internal surfaces of mounting collar 62 and may create a seal therein. Locking sleeve 66 incorporates corresponding internal threaded 68 (shown in cut-away) adjacent its proximal end. Once connector assembly is positioned with respect to lumens of catheter member 14 and internal passages of catheter hub 12, locking sleeve 66 and catheter member 14 are advanced toward catheter hub 12 to approximate locking sleeve 66 and mounting collar 62 of the catheter hub 12. Thereafter, locking sleeve 66 is rotated whereby the corresponding threaded components 64, 68 of locking sleeve 66 and mounting collar 62 cooperate to secure the locking sleeve 66 to catheter hub 12. Locking sleeve 66 may have an internal dimension to compress elastomeric first collar segment 60a of grommet 60 thereby creating an interference relationship between the locking sleeve 66 and connector tubes 42 and also facilitating the formation of a seal within catheter hub 12.

FIGS. 10-11 illustrate another embodiment of the present disclosure. In accordance with this embodiment, catheter hub 70 incorporates mounting collar 72 which possesses first and second longitudinal grooves 74 arranged in opposed relation. Catheter hub 70 also incorporates first and second hypo tubes 76 which may be fixed within the catheter hub 70. Locking sleeve 78 mounted about catheter member 14 incorporates first and second axially depending locking tabs 80. Locking tabs 80 each incorporate locking detents 82. Upon assembly, locking tabs 80 are positioned within first and second longitudinal grooves 74 of catheter hub 70 with locking detents 82 of the locking tabs 80 securely engaging proximally facing shelves 84 of mounting collar 72 to secure locking sleeve 78 and catheter hub 70. Locking sleeve 78 may incorporate internal structure to compress the proximal end of catheter 14 against the hypo tubes. Alternatively, the lumens of catheter member 14 may be dimensioned to form a friction fit about the hypo tubes 76. Locking sleeve 78 and/or locking tabs 80 may be rigid such that securement of the locking tabs 80 to the catheter hub 70 may be irreversible. This may prevent disconnection by the patient.

Figure 12A:
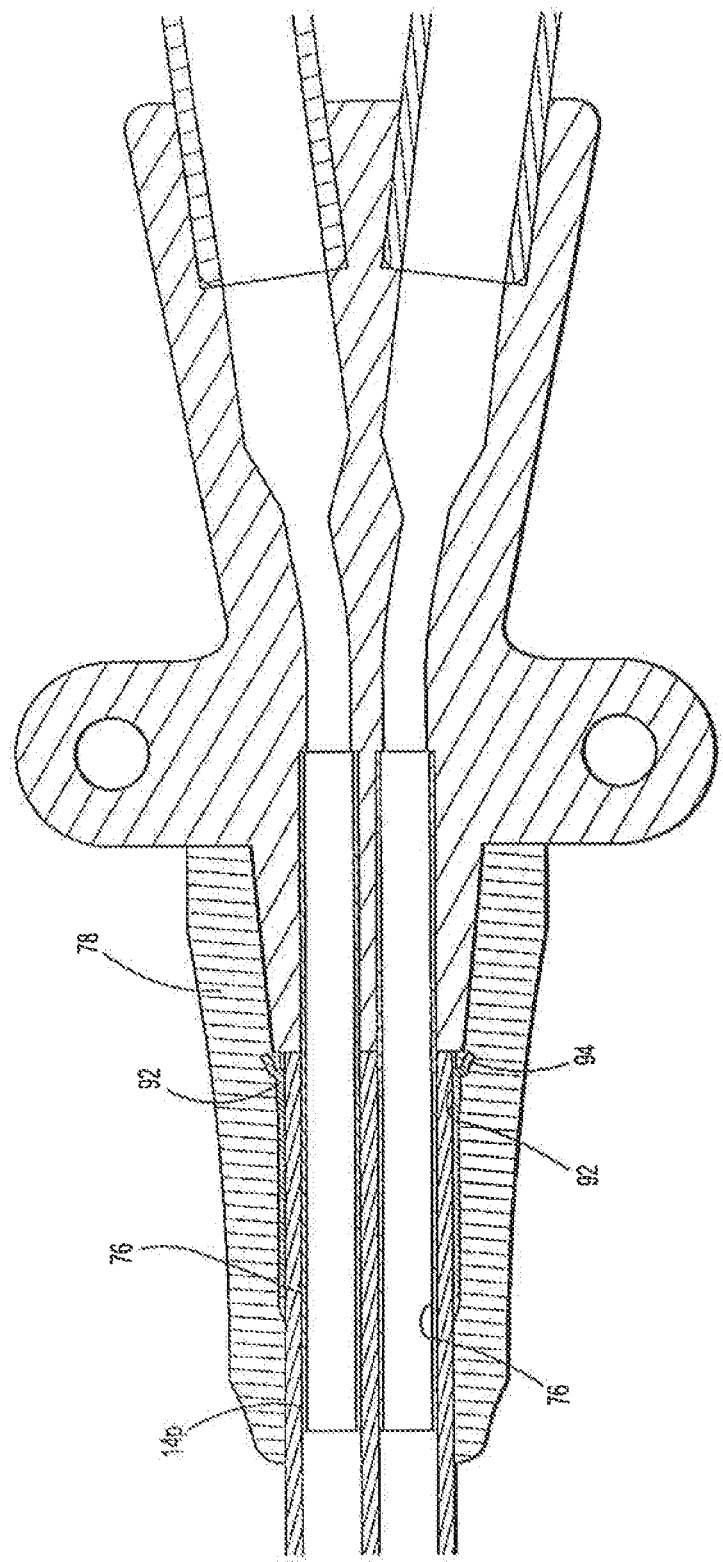
FIG. 12A is a side cross-sectional view of the catheter system of FIG. 12.

FIGS. 12, 12A and 13 illustrate another embodiment generally similar to the embodiment of FIGS. 10-11. However, in accordance with this embodiment, a compressible member or ring 90 is positioned about the proximal end of catheter member 14 prior to securement of locking sleeve 78. Compressible ring 90 is preferably made of spring metal or the like and has a plurality of radially spaced deflectable elements 91. Each deflectable element 91 has edge 92 which may engage the proximal end of catheter member 14 to assist in securing catheter member 14 to the hypo tubes 76. Compressible ring 90 is deflected inwardly during securement of locking sleeve 78 to catheter hub 12 as best depicted in FIG. 12A through engagement of outer ramp surfaces 94 of the deflectable elements 91 and the interior of locking sleeve 78.

FIG. 12B shows an alternate embodiment with a deflecting ring 93 positioned around the proximal end of the catheter 14. The deflecting ring 93 compresses and seals the catheter 14 once locking sleeve 78 is advanced in a proximal direction toward the catheter hub 70. The radial compression exerted by the deflecting ring 93 on the catheter 14 grips the catheter 14 to the first and second hypo tubes 76, thereby retaining the catheter 14 connected to the catheter hub 70. Deflecting ring 93 includes ring collar 93a and compressing segment 93b extending from the ring collar 93a. Compressing segment 93b includes axial slots 93c which permit inward deflection of the compressing segment 93b. Ring collar 93a may have a recess 93d for receiving a corresponding tab 72a of mounting collar 72 of catheter hub 70. This arrangement may facilitate securement of deflecting ring 93 relative to catheter hub 70.

FIGS. 14-16 illustrate another embodiment of the catheter hub attachment mechanism. In accordance with this embodiment, hypo tubes or connector tubes 90 are mounted to extend from catheter hub 92. Catheter member 14 is advanced over the connector or hypo tubes 90 to essentially abut against the distal face of catheter hub 92. Locking sleeve 94 is pushed or advanced over the proximal end 14p of catheter member 14 whereby locking detent 96 of the locking sleeve 94 engages corresponding annular ridge 98 of catheter hub 92 to secure the locking sleeve 94 to the catheter hub 92. As a further feature, the internal surface of locking sleeve 94 may incorporate interference areas 100 which extend radially inwardly. The interference areas 100 serve to compressibly engage the outer surface of catheter member 14 to establish an interference relation therewith. Locking sleeve 94 may be formed of a suitable elastomeric material to expand and contract to permit positioning over catheter hub.

Figure 19:
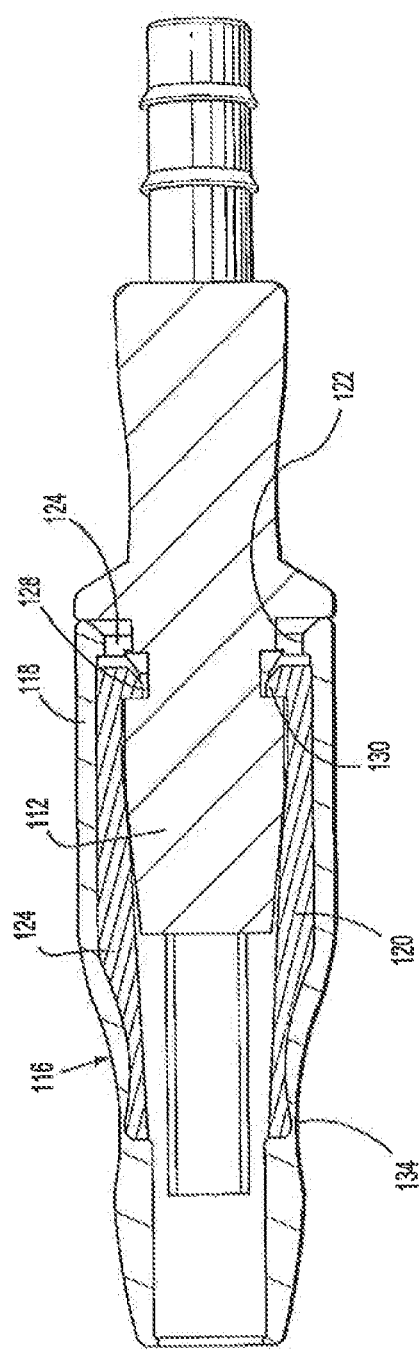
FIG. 19 is a side cross-sectional view of the catheter hub of the catheter system of FIGS. 17-18.

FIGS. 17-19 illustrate another embodiment of the hub attachment mechanism. Catheter hub 110 includes tapered mounting collar 112 and annular shelf 114 adjacent a proximal end of the mounting collar 112. Locking sleeve 116 incorporates several components which permit releasable attachment of locking sleeve 116 to catheter hub 110. Specifically, locking sleeve 116 includes outer locking member 118 and inner locking member 120. Outer member 118 may be elastomeric and encloses inner member 120 and the proximal end 14p of catheter member 14. Outer member 118 may have an internal annular detent 122 at its trailing end which is received within a corresponding outer annular recess 124 of catheter hub 110 to secure the outer member 120 to the catheter hub 110. Inner member 112 includes opposed locking legs 124 which are interconnected by partial ring 126 extending between the legs 124. Locking legs 124 are adapted for pivotal movement relative to rings 126 upon depression of leading leg elements 124l. This action will cause trailing leg elements 124t to pivot radially outwardly out of engagement with corresponding locking recesses 128 in mounting collar 112 of catheter hub 110. In use, catheter member 14 is positioned about the hypo or connecting tubes extending from catheter hub 112. Thereafter, locking sleeve 116 is advanced to resiliently and/or frictionally engage the outer surface of catheter member 14. When appropriately positioned, trailing or proximal leg elements 124t are positioned whereby locking detents 130 of the leg elements are received within locking recesses 128 of mounting collar 120. Similarly, internal annular detent 122 of outer member 118 is secured within annular recess 124 of catheter hub 110. With this arrangement, locking sleeve 116 and catheter member 14 are secured to catheter hub 110. When it is desired to release catheter hub 110 from catheter member 14, outer member 118 is depressed adjacent finger grooves 134 which causes engagement with the leading or distal leg elements 124l of locking legs 124. Further squeezing movement causes, proximal or trailing leg elements 124t to pivot outwardly and become released from locking recesses 128. Catheter member 14 may then be moved from catheter hub 110.

FIGS. 20-22 illustrate another alternate embodiment of the catheter hub attachment mechanism. In accordance with this embodiment, locking sleeve 150 includes first 152 and second series 154 of internal threads. The first series 152 is adapted to threadably engage the outer threaded surface 156 of mounting collar of catheter hub 158. The second series 154 engages the proximal end of catheter tube 14 when the locking sleeve 150 is secured to the catheter hub 158. In one aspect of this embodiment, hypo tubes 160 extending from catheter hub 158 may be slightly larger in diameter or dimension than internal lumens of the catheter 14. Thus upon passage of the catheter proximal end 14p over the respective hypo tubes 160, the catheter must stretch to some degree to accommodate the hypo tubes 160. Thus upon securing of locking sleeve 150, the second series of threads 154 more readily bites into the catheter proximal end 14p securing the catheter 14 relative to the hypo tubes and the hub.

FIGS. 23-25 illustrate another embodiment which is substantially similar to the prior embodiment. In accordance with this embodiment, however, the connection tubes or hypo tubes define a dimension which increases in cross section toward catheter hub, i.e., has an outward flare adjacent catheter hub. This configuration may facilitate initial positioning of proximal catheter end onto the connection tubes whereby upon continued movement toward catheter hub, the wider dimension of the hypo tubes contacts the proximal end of the catheter, e.g., in frictional engagement therewith. In addition, upon tightening of locking sleeve, the internal threads in effect obtain a larger bite of the catheter adjacent catheter hub at the flared areas further securing the catheter on the hub.

FIG. 26 has an alternate embodiment of catheter hub which may be utilized with the embodiments of FIGS. 20-25. In this embodiment, instead of the hypo tubes having a flared aspect, catheter hub incorporates flared areas or molded projections 180 extending from hub mounting collar. Thus upon advancement of catheter proximal end, the proximal end will widen adjacent catheter hub. This enables locking sleeve, e.g., the second series of threads 154 to engage the catheter at the extreme proximal end adjacent the hub mounting collar.

Figure 29:
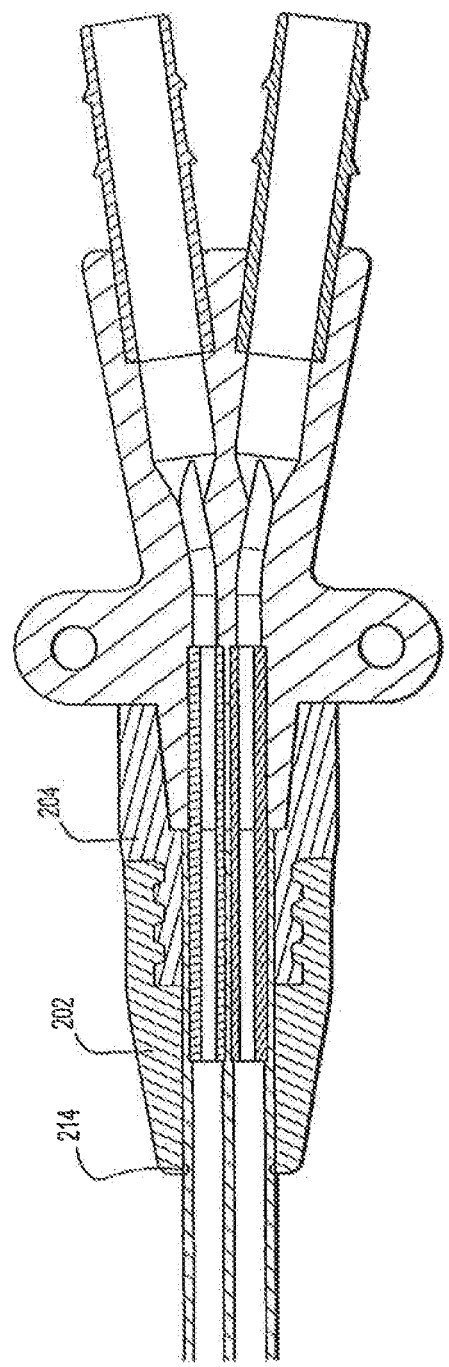
FIG. 29 is a side cross-sectional view of the catheter hub of FIG. 27 illustrating the securing of the catheter member.

FIG. 27-29 illustrate an alternate embodiment where locking sleeve 200 includes two interconnected components, namely, distal elastomeric component 202 and relatively rigid proximal component 204. Rigid component 204 incorporates opposed locking tabs 206 and detents 208 receivable within locking grooves 210 of catheter hub in a similar manner to the embodiment of FIG. 11. Elastomeric component 202 is adapted to form a seal about catheter member adjacent the extreme distal or leading end of the elastomeric component. The seal may incorporate a radially inwardly directed annular projection 214 or the like. The seal may minimize the passage of fluids through locking sleeve.

Figure 29B:
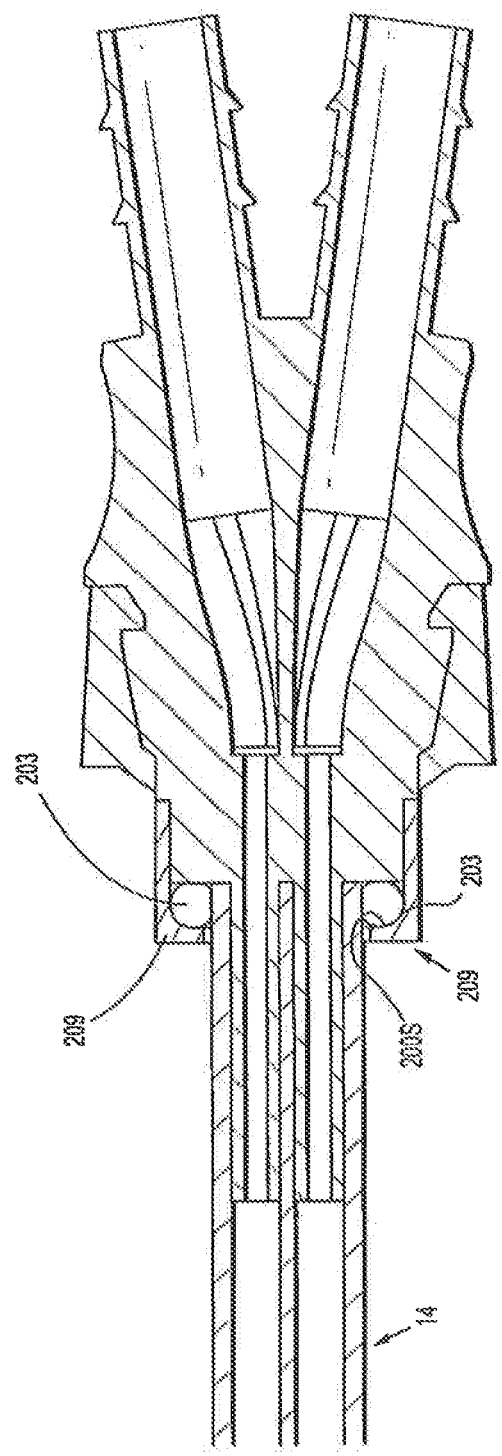
FIG. 29B is a side cross-sectional view of an alternate embodiment of the catheter system.

FIG. 29A illustrates an alternate embodiment incorporating O-ring 203. As locking sleeve 200 advances proximally over the first and second hypo tubes 205, 207, the locking sleeve 200 radially compresses the O-ring 203 between an internal shelf 200S of the locking sleeve and the distal or leading face 112a of catheter hub 110. The compressed O-ring 203 secures catheter 14 to catheter hub 110. O-ring 203 may be made of soft material, an elastomer, a rigid material, or any other suitable material. In an alternate embodiment depicted in FIG. 29B, internal shelf 200S of locking sleeve 200 is adjacent the distal or leading end of the locking sleeve 200.

Figure 29C:
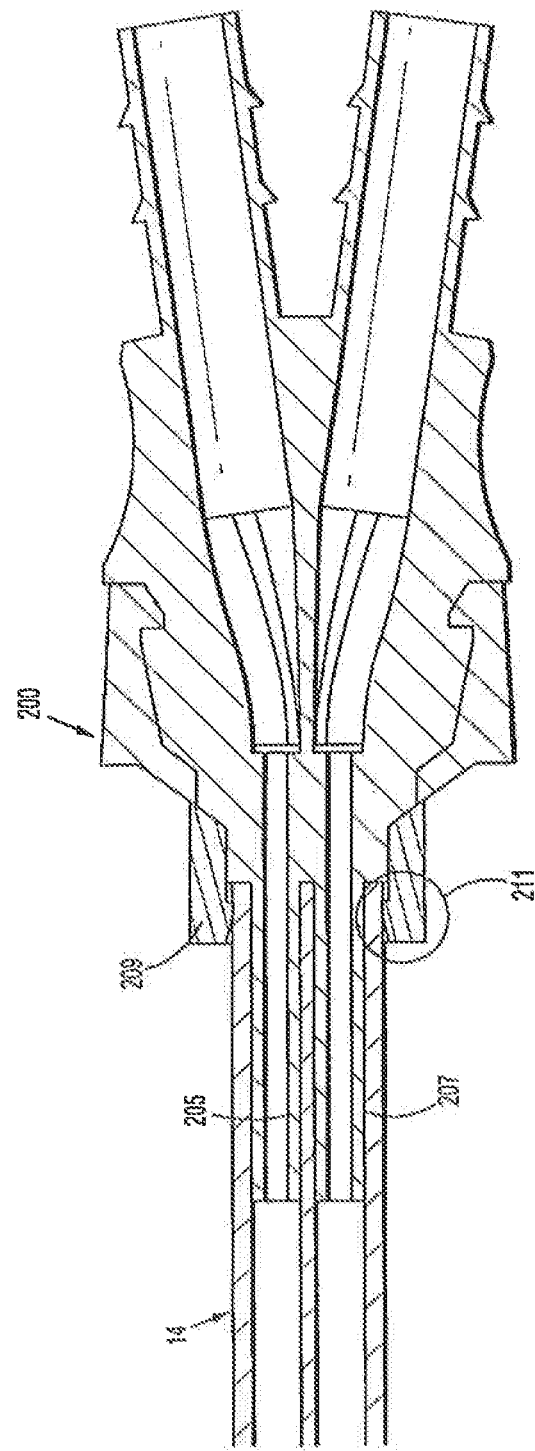
FIG. 29C is a side cross-sectional view of an alternate embodiment of the catheter system.
Figure 29D:
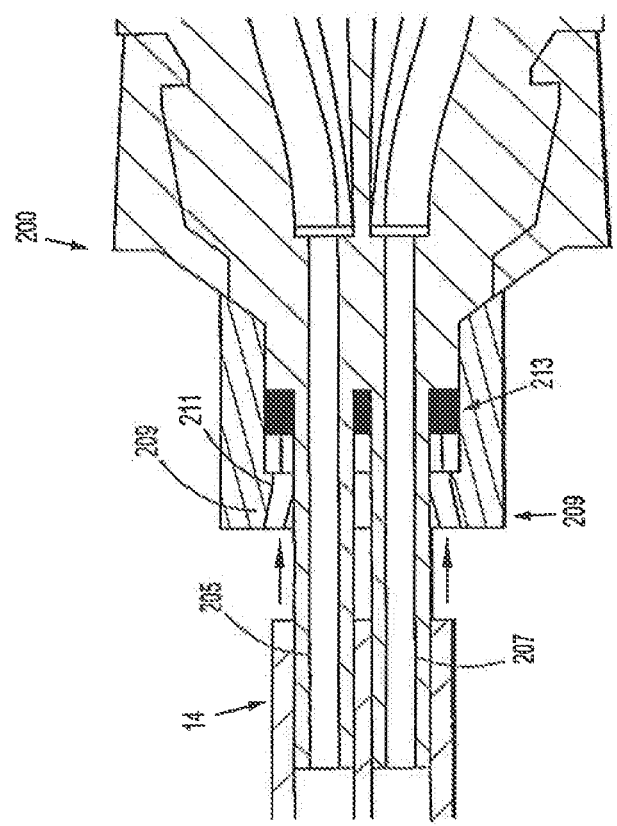
FIG. 29D is a side cross-sectional view of the catheter hub of FIG. 29C separated from the catheter.
Figure 29E:
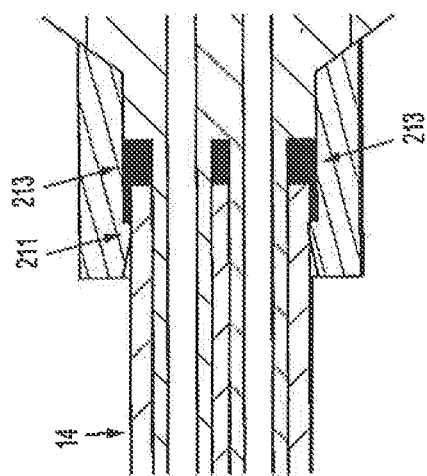
FIG. 29E is a side cross-sectional view of the catheter hub of FIG. 29C coupled to the catheter.
Figure 31:
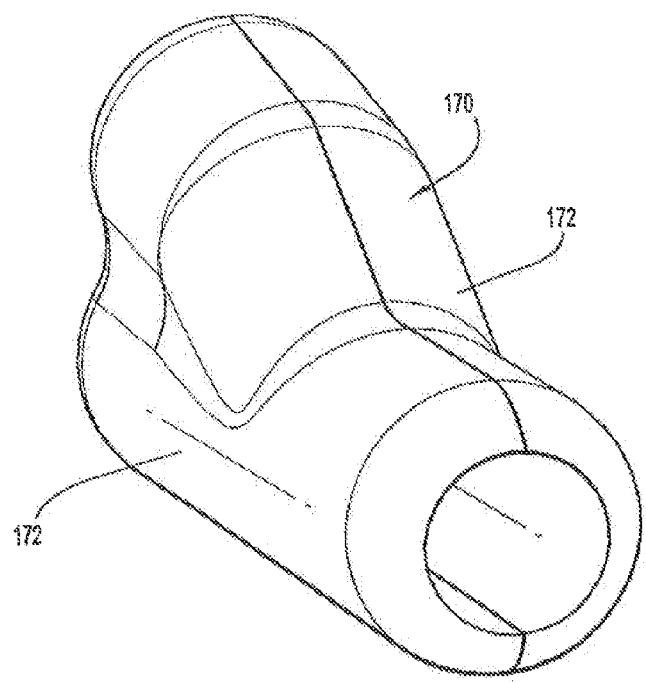
FIG. 31 is a perspective view of an alternate embodiment of a catheter system.
Figure 32:
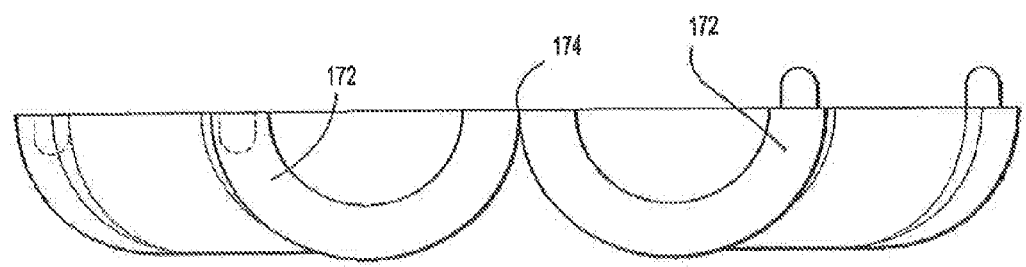
FIG. 32 is a perspective view of the catheter hub of the embodiment of FIG. 31 in an open position.

FIG. 29C depicts an alternative embodiment of the locking sleeve 200. Iii this embodiment, locking sleeve 200 includes a housing 209 extending distally therefrom. The housing 209 incorporates rigid detents 211 adapted to compress the catheter 14 against the hypo tubes 205, 207. Rigid detents 211 are biased inwardly with respect to the catheter 14. The radial compression exerted by the rigid detents 211 secures the catheter 14 to the catheter hub. The housing 209 may include radial gaps to facilitate assembly and enhance grip. Additionally, the housing 209 may be clear to facilitate visualization of the position of the catheter 14 when the catheter 14 is advanced toward the catheter hub. As illustrated in FIGS. 29D and 29E, the housing 209 of locking sleeve 200 may further include an adhesive 213 therein. The adhesive 213 attaches the catheter 14 to the locking sleeve 200 and may compress the catheter 14 to form a fluid tight seal. After the proximal end of the catheter 14 is positioned within the housing 209, the adhesive 213 seals and attaches catheter 14 to the catheter hub. At the same time, the rigid detents 211 of the housing 209 compress the catheter 14 against the hypo tubes 205, 207, thereby securing the catheter 14 to the catheter hub. Adhesive 213 may be any suitable kind of adhesive including, but not limited to, an adhesive hydrogel.

FIG. 30 illustrates an alternate embodiment where locking sleeve 220 and hypo tubes 222 have a similar sloped, angled or arcuate surface 224, 226. This angled surface may enhance the interference relationship of the locking sleeve 220 with t the catheter tube.

FIGS. 31-34 illustrate another catheter hub 170 consisting of two half shells 172 connected to each other through a hinge 174. The interior of the catheter hub 170 has arcuate recesses 176 which capture an outer ring 178 attached to the proximal end 14p of the catheter 14. In use, the proximal catheter end 14p is positioned within the open catheter hub 170 with the ring 178 seated within one recess 176 of the half shell. The other half shell is folded onto the half shell and can be connected thereto via a snap fit or the like such as the pin and hole 180, 182 arrangement shown. With the catheter ring 178 secured within the recess 176 of the catheter hub 170 the catheter is thereby secured to the hub 170.

The use of any of the aforementioned catheter systems will now be discussed in connection with a subcutaneous tunneling procedure for hemodialysis. With reference to FIG. 35, the leading or distal end of the catheter may be implanted within a major vein of a patient via the reverse tunneling method disclosed in U.S. Pat. No. 5,509,897 to Twardowski, the entire contents of the '897 patent being incorporated herein by reference. In accordance with one embodiment of this procedure disclosed in the '897 patent, a catheter 14 is positioned through an incision "i" made beneath the clavicle, and advanced to enter the right atrium "ra". A surgical tunnel is then created from the initial incision "i" outwardly to an exit site "e" remote from the original incision "i". Alternatively, the surgical tunnel may be created from the exit site "e" to the initial incision "i." A proximal section 14p of the catheter 14 is advanced through the tunnel and out through the exit site "e". With the proximal end of the catheter exposed, any of the aforementioned hub attachments mechanisms may be employed to attach the catheter hub to the catheter. Thereafter, the venous and arterial lines are connected to the catheter hub as is conventional.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A hemodialysis catheter assembly comprising:
   a catheter hub including a first section, a second section, and a hinge connecting the first section to the second section, the first section and the second section movable relative to each other between open and closed positions, the catheter hub defining a first fluid channel and a second fluid channel when the first and second sections of the catheter hub are in the closed position, wherein each of the first section and the second section defines a portion of the first fluid channel and the second fluid channel; and
   an elongated catheter defining a first catheter lumen and a second catheter lumen, the elongated catheter having a leading end and a trailing end, wherein the trailing end of the elongated catheter is positionable within one of the first and second sections of the catheter hub when the first and second sections of the catheter hub are in the open position, and the trailing end of the elongated catheter is secured between the first section and the second section of the catheter hub upon movement of the first section and the second section of the catheter hub to the closed position such that the first catheter lumen is in fluid communication with the first fluid channel and the second catheter lumen is in fluid communication with the second fluid channel.

2. The catheter assembly of claim 1, wherein the hinge defines a hinge axis parallel to the first catheter lumen and the second catheter lumen when the trailing end of the elongated catheter is secured between the first section and the second section of the catheter hub.

3. The catheter assembly of claim 1, wherein the first section of the catheter hub defines a first arcuate recess and the second section of the catheter hub defines a second arcuate recess, the elongated catheter further comprises a ring supported on an outer surface of the elongated catheter, adjacent the trailing end of the elongated catheter, the arcuate recesses of the first section and the second section of the catheter hub retaining the ring when the first and second sections of the catheter hub are in the closed position.

4. The catheter assembly of claim 3, wherein the first arcuate recess of the first section of the catheter hub and the second arcuate recess of the second section of the catheter hub define an annular recess when the first and second sections of the catheter hub are in the closed position.

5. The catheter assembly of claim 1, wherein at least one of the first section and the second section of the catheter hub includes a securement feature that facilitates the securement of the first section and the second section to one another when the first section and the second section are in the closed position.

6. The catheter assembly of claim 5, wherein the first section of the catheter hub includes a pin and the second section of the catheter hub includes a hole, the pin being receivable in the hole in a snap-fit arrangement to secure the first section and the second section relative to one another in the closed position.

7. A catheter hub for a hemodialysis catheter assembly, the catheter hub comprising:
a first section and a second section connected by a hinge, at least one of the first section and the second section pivotal about the hinge relative to the other section to reposition the first section and the second section relative to one another, wherein the first section and the second section are pivotal from an open position to a closed configuration to selectively mount the first section and the second section to a trailing end of an elongated catheter, the first section and the second section defining a first fluid channel and a second fluid channel when disposed relative to one another in the closed position.

8. The catheter hub of claim 7, wherein each of the first section and the second section define an arcuate recess, the arcuate recesses forming an annular recess when the first section and the second section are disposed in relative to one another in the closed position.

9. The catheter hub of claim 7, wherein at least one of the first section and the second section includes a securement feature that facilitates the securement of the first section and the second sections to one another in the closed position.

10. The catheter hub of claim 9, wherein the first section includes a pin and the second section includes a hole, the pin receivable within the hole in a snap-fit arrangement to secure the first section and the second section relative to one another in the closed position.

11. The catheter hub of claim 7, wherein at least a portion of the second channel is non-parallel to the first channel.

12. The catheter hub of claim 7, wherein at least a portion of each of the first channel and the second channel has a non-uniform cross-sectional area.

* * * * *